United States Patent
Küppers-Munther et al.

(10) Patent No.: US 10,202,579 B2
(45) Date of Patent: Feb. 12, 2019

(54) METHODS FOR PRODUCING MAMMALIAN PLURIPOTENT STEM CELL-DERIVED ENDODERMAL CELLS

(71) Applicant: Takara Bio Europe AB, Göteborg (SE)

(72) Inventors: Barbara Küppers-Munther, Göteborg (SE); Josefina Edsbagge, Torslanda (SE)

(73) Assignee: Takara Bio Europe AB, Gothenburg (SE)

( * ) Notice: Subject to any disclaimer, the term of this patent is extended or adjusted under 35 U.S.C. 154(b) by 0 days.

(21) Appl. No.: 14/648,336

(22) PCT Filed: Nov. 28, 2013

(86) PCT No.: PCT/EP2013/075018
§ 371 (c)(1),
(2) Date: May 29, 2015

(87) PCT Pub. No.: WO2014/083133
PCT Pub. Date: Jun. 5, 2014

(65) Prior Publication Data
US 2016/0304834 A1    Oct. 20, 2016

Related U.S. Application Data

(60) Provisional application No. 61/731,241, filed on Nov. 29, 2012.

(30) Foreign Application Priority Data

Nov. 29, 2012 (DK) .................................. 2012 70739

(51) Int. Cl.
C12N 5/074 (2010.01)
C12N 5/0735 (2010.01)
C12N 5/071 (2010.01)

(52) U.S. Cl.
CPC ......... C12N 5/0607 (2013.01); C12N 5/0606 (2013.01); C12N 5/067 (2013.01); C12N 2501/06 (2013.01); C12N 2501/16 (2013.01); C12N 2501/70 (2013.01); C12N 2501/727 (2013.01); C12N 2501/999 (2013.01); C12N 2506/02 (2013.01); C12N 2506/03 (2013.01); C12N 2506/45 (2013.01)

(58) Field of Classification Search
CPC .... C12N 5/0607; C12N 5/0606; C12N 5/067; C12N 2501/06; C12N 2501/16; C12N 2501/70; C12N 2501/727; C12N 2501/999; C12N 2506/02; C12N 2506/03; C12N 2506/45
USPC ......................................................... 435/366
See application file for complete search history.

(56) References Cited

U.S. PATENT DOCUMENTS

| | | | |
|---|---|---|---|
| 2005/0054092 A1 | 3/2005 | Xu et al. | |
| 2007/0196514 A1 | 8/2007 | Li | |
| 2009/0053182 A1 | 2/2009 | Ichim et al. | |
| 2010/0143313 A1 | 6/2010 | Yarmush et al. | |
| 2010/0166713 A1 | 7/2010 | Dalton et al. | |
| 2010/0173414 A1* | 7/2010 | Turovets .............. | C12N 5/0603 435/377 |

FOREIGN PATENT DOCUMENTS

| | | |
|---|---|---|
| JP | 2004-535199 A | 11/2004 |
| WO | 2003/006950 A2 | 1/2003 |
| WO | 2007/058105 A1 | 5/2007 |
| WO | 2010/065679 | 6/2010 |
| WO | 2011116930 A1 | 9/2011 |

OTHER PUBLICATIONS

Yoon et al., Enhanced differentiation of human embryonic stem cells into cardiomyocytes by combining hanging drop culture and 5-azacytidine treatment, Differentiation (2006) 74: 149-159.*
International Search Report and Written Opinion for Application PCT/EP2013/075018 dated Feb. 3, 2014.
Kim et al., "Epigenetic signatures and temporal expression of lineage-specific genes in hESCs during differentiation to hepatocytes in vitro," Human Molecular Genetics, Feb. 1, 2011, vol. 20, No. 3, pp. 401-412.
Kim et al., Differentiation of Mouse Embryonic Stem Cells into Endoderm without Embryoid Body Formation,: PLOS One, Jan. 1, 2010, vol. 5, No. 11, p. e14146.
Pennarossa et al., "Brief demethylation step allows the conversion of adult human skin fibroblasts into insulin-secreting cells," Proceedings of the National Academy of Sciences, May 21, 2013, vol. 110, No. 22, pp. 8948-8953.
Saswati et al., "DNA methylthansferase inhibition induces mouse embryonic stem cell differentiation into endothelial cells," Experimentation Cell Research, Jan. 15, 2010, vol. 312, No. 2, pp. 172-180.
Wang et al., "Generating cells of the gastrointestinal system: current approaches and applications for the differentiation of human pluripotent stem cells," Journal of Molecular Medicine, Springer, Berlin, DE, Jun. 20, 2012, vol. 90, No. 7, pp. 763-771.

(Continued)

Primary Examiner — Jennifer M. H. Tichy
(74) Attorney, Agent, or Firm — Fox Rothschild LLP

(57) ABSTRACT

The present invention relates to the directed differentiation of mammalian pluripotent stem cells, especially human pluripotent stem (hPS) cells, into endodermal cells. In particular, the present invention relates to the treatment of mammalian pluripotent stem cells, especially hPS cells, with a DNA demethylating agent while undergoing differentiation into endodermal. The inventors have, as disclosed herein, found that exposing differentiating mammalian pluripotent stem cells, especially hPS cells, to a DNA demethylating agent leads to an improved morphology and improved yield of endodermal cells. The treatment with a DNA de-methylating agent also leads to a significant down-regulation of expression of the stem cell marker Oct4 and to an improved expression of endoderm specific markers, notably sox17, cxcr4 and hhex.

24 Claims, 12 Drawing Sheets

(56) References Cited

OTHER PUBLICATIONS

Wei et al., "Histone H3K27me3 demethylases KDM6A and KDM6B modulate definitive endoderm differentiation from human ESCs by regulating WNT signaling pathway," Cell Research, Aug. 21, 2012, vol. 23, No. 1, pp. 122-130.
Falasca et al., The effect of retinoic acid on the re-establishment of differentiated hepatocyte phontype in primary culture, Cell Tissue Res (1998); 293:337-347.
Si-Tayeb et al., "Highly Efficient Generation of Human Hepatocyte-Like Cells from induced Pluripotent Stem Cells," Heptaology (Jan. 2010); 51:297-305.
International Search Report and Written Opinion for Application PCT/EP2013/075017 dated Apr. 25, 2014.
Behbahan et al., "New approaches in the differentiation of human embryonic stem cells and induced pluripotent stem cells toward hepatocytes," Stem Cell Reviews, Sep. 2011, vol. 7, No. 3, pp. 748-759.
Cai et al., "Retinoic acid represses CYP7A1 expression in human hepatocytes and HepG2 cells by FXR/RXR-dependent and independent mechanisms," Journal of Lipid Research, Aug. 2010, vol. 51, No. 8, pp. 2265-2274.
Huang et al., "Retinoic acid signalling induces the differentiation of mouse fetal liver-derived hepatic progenitor cells," Liver International: Official Journal of the International Association for the Study of the Liver, Nov. 2009, vol. 29, No. 10, pp. 1569-1581.
Ishii et al., "Effects of extracellular matrixes and growth factors on the hepatic differentiation of human embryonic stem cells," American Journal of Physiology, Gastrointestinal and Liver Physiology, Aug. 2008, vol. 295, No. 2, pp. G313-G321.
Touboul et al., "Generation of functional hepatocytes from human embryonic stem cells under chemically defined conditions that recapitulate liver development," Hepatology (Baltimore, MD), May 2010, vol. 51, No. 5, pp. 1527-1765.
Yu et al., "Hepatocyte-like cells differentiated from human induced pluripotent stem cells: relevance to cellular therapies," Stem Cell Research, Nov. 2012, vol. 9, No. 3, pp. 196-207.
Zhang et al., "Generation characterization and potential therapeutic applications of mature and functional hepatocytes from stem cells," Journal of Cellular Physiology Feb. 2013, Jun. 27, 2012, vol. 228, No. 2, pp. 298-305.
Zhao et al., "Promotion of the efficient metabolic maturation of human pluripotent stem cell-derived hepatocytes by correcting specification defects," Cell Research, Oct. 16, 2012, vol. 23, No. 1, pp. 157-161.

* cited by examiner

Fig. 1A-1) control             Fig. 1A-2) 10nM 5aza-dC d2-3
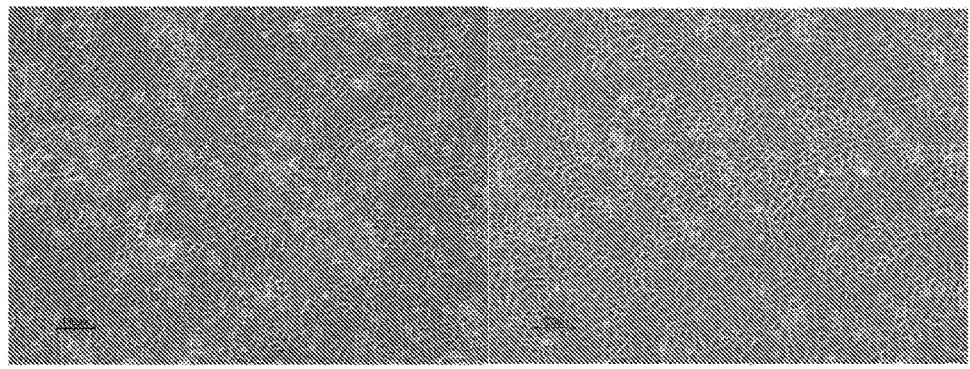
Fig. 1B-1) control             Fig. 1B-2) 10nM 5aza-dC d2-3
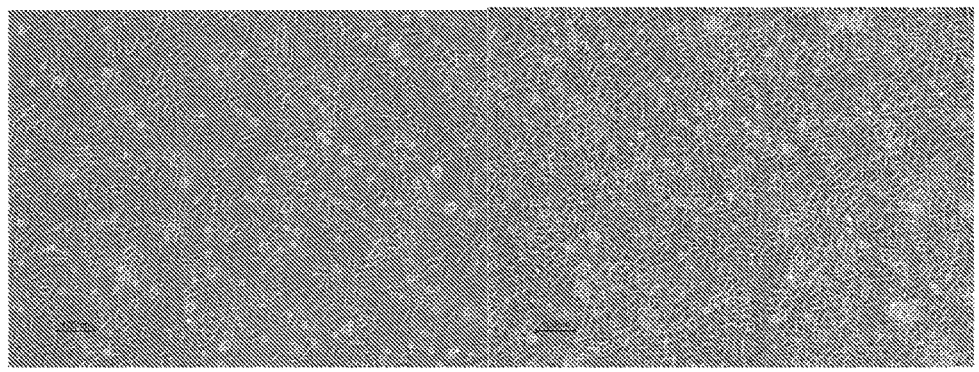

Fig. 1C-1) control: Oct4-immunstaining and DAPI nuclear staining
Fig. 1C-2) 10nM 5aza-dC d2-3: Oct4-immunstaining and DAPI nuclear staining
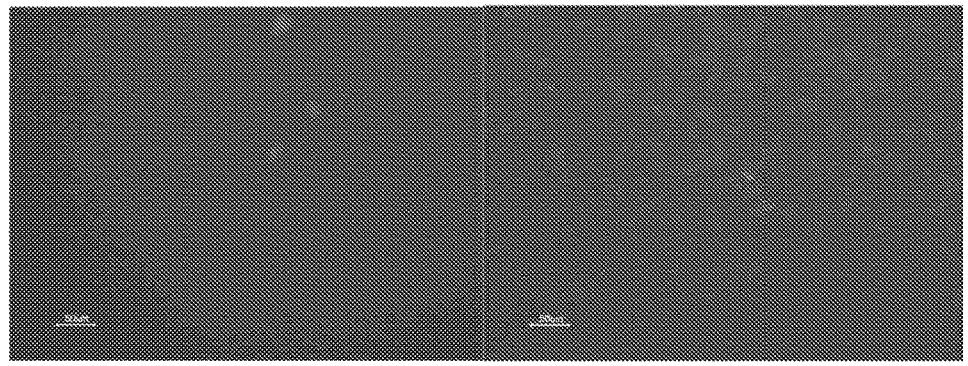

METHODS FOR PRODUCING MAMMALIAN PLURIPOTENT STEM CELL-DERIVED ENDODERMAL CELLS

CROSS REFERENCE TO RELATED APPLICATIONS

This application is the U.S. National Phase filing of PCT International Application No. PCT/EP2013/0075018, filed Nov. 28, 2013, which claims priority to Denmark Application No. PA201270739, filed Nov. 29, 2012 and U.S. Provisional Patent Application No. 61/731,241, filed Nov. 29, 2012. The contents of the foregoing applications are incorporated herein by reference in their entireties.

TECHNICAL FIELD

The present invention relates to the directed differentiation of mammalian pluripotent stem cells, especially human pluripotent stem (hPS) cells, into cells of the definitive endoderm. In particular, the present invention relates to the treatment of mammalian pluripotent stem cells, especially hPS cells, with a DNA demethylating agent while undergoing differentiation into endoderm. The present inventors have, as disclosed herein, found that exposing differentiating mammalian pluripotent stem cells, especially hPS cells, to a DNA demethylating agent leads to an improved morphology and improved yield of endodermal cells. The treatment with a DNA demethylating agent also leads to a significant down-regulation of expression of the stem cell marker Oct4 and to an improved expression of endoderm specific markers, notably sox17, cxcr4 and hhex.

BACKGROUND OF THE INVENTION

Human pluripotent stem cells are expected to revolutionize the accessibility to a variety of human cell types since they have the capacity, under appropriate conditions, to self-renew as well as the ability to form any type of specialized cells of the three germ layers (endoderm, mesoderm, and ectoderm). Of major interest is the endodermal layer since it gives rise to the intestine, pancreas, liver and lung, i.e. organs of the human body failure or damage of which are associated with a great number of disease states and clinical disorders seen today. A great promise thus lies in the in vitro development of organ specific tissue for replacement therapy.

Due to its unique capability among the three germ layers to develop into the above mentioned organs, the endoderm, more specifically the definitive endoderm, plays a central role in the production of organ specific tissue. Thus, there is a constant need to improve the characteristics of in vitro derived endodermal cells which eventually has an impact on the quality and quantity of the organ specific cells and tissue. However, early endoderm development is not well understood, with only a few factors so far identified to drive the differentiation of human pluripotent stem cells towards endoderm. Accordingly, finding further, yet unidentified, factors having an influence on endodermal development is important and will help to optimize the cultivation condition for in vitro production of cells and tissue of endodermal organs.

The importance of DNA methylation during normal embryogenesis and development has long been suspected and the application of DNA demethylating agents can cause reactivation of large swathes of genes in a genome. Previous work has shown that DNA demethylation can be used to direct differentiation of hES cells towards cardiac fate (Yoon et al 2006), presumably by activating genes required for cardiomyogenesis which would normally be methylated and silenced.

SUMMARY OF THE INVENTION

The present invention describes improved methods by which mammalian pluripotent stem cells, especially human pluripotent stem (hPS) cells, are differentiated into cells of the definitive endoderm, which possess improved characteristics compared to endodermal cells obtained by currently available state of the art methods.

The present invention provides in a first aspect a method for producing mammalian pluripotent stem cell-derived cells of the definitive endoderm (DE cells), especially human pluripotent stem (hPS) cell-derived cells of the definitive endoderm (DE cells), wherein mammalian pluripotent stem cells, especially human pluripotent stem cells, are exposed to a DNA demethylating agent.

Thus, a method for producing mammalian pluripotent stem cell-derived DE cells is provided which comprises:
 Culturing mammalian pluripotent stem cells under differentiation conditions to obtain DE cells, and
 Exposing the differentiating mammalian pluripotent stem cells to a DNA demethylating agent.

Especially, a method for producing human pluripotent stem (hPS) cell-derived DE cells is provided which comprises:
 Culturing human pluripotent stem cells under differentiation conditions to obtain DE cells, and
 Exposing the differentiating human pluripotent stem cells to a DNA demethylating agent.

During the differentiation of mammalian pluripotent stem cells, especially hPS cells, into definitive endodermal cells, the differentiating mammalian pluripotent stem cells, especially hPS cells, are exposed to a DNA demethylating agent, such as 5-aza-2-deoxycytidine or 5-azacytidine, to demethylate sections of the genome and allow transcriptional activation of genes.

The exposure to said DNA demethylating agent may take place at any time during the differentiation of the mammalian pluripotent stem cells, especially hPS cells, into DE cells.

As a result of the methods according to the present invention, cells of the definitive endoderm and cell compositions comprising the same are obtained having improved characteristics. Thus, in further aspects, the invention relates to a definitive endodermal cell(s) obtained by the method of the invention and to a cell composition(s) comprising, or consisting of, said endodermal cell(s), In another aspect, the present invention relates to the further use of the definitive endodermal cell(s) or cell composition(s) of the invention for producing cells or tissue of the intestine, pancreas, liver and/or lung. The definitive endodermal cell(s) or cell composition(s) of the invention, may, for instance, be used to produce hepatic progenitor cells or fully matured hepatocyte-like cells, including hepatic tissue. The definitive endodermal cell(s) or cell composition(s) of the invention, may also be used to produce pancreatic precursor cells or fully matured pancreatic cells, such as pancreatic stellate cells or Langerhans cells, or pancreatic tissue.

In other aspects, the invention provides the further uses of the definitive endodermal cell(s) or cell composition(s) of the invention in pharmaceutical and toxicological screening, such as drug discovery processes or toxicity testing.

In a further aspect, the present invention provides the use of a DNA demethylating agent in the production of cells of the definitive endoderm from mammalian pluripotent stem cells, especially human pluripotent stem cells.

In yet a further aspect, the invention relates to kits useful in carrying out the methods of the invention. Included in this aspect are kits which comprise at least one DNA demethylating agent. It is understood that the details given herein with respect to the components employed in the methods of the invention also apply to the components comprised by the kits of the invention.

In yet a further aspect, the invention relates to compositions. Such compositions are particularly useful for producing cells of the definitive endoderm from mammalian pluripotent stem cells, especially human pluripotent stem. Included in this aspect are compositions which comprise at least one DNA demethylating agent and activin, such as activin A or B. It is understood that the details given herein with respect to the components employed in the methods of the invention also apply to the components comprised by the compositions of the invention.

DETAILED DESCRIPTION OF THE INVENTION

The present invention provides methods for differentiating mammalian pluripotent stem cells, especially human pluripotent stem cells, into cells of the definitive endoderm, the method comprising culturing said mammalian pluripotent stem cells, especially hPS cells, in a supportive culture and differentiation medium containing a DNA demethylating agent. The mammalian stem cells, especially hPS cells, while undergoing differentiation into endoderm are thus exposed to a DNA demethylating agent.

Accordingly, the present invention provides a method for producing cells of the definitive endoderm from mammalian pluripotent stem cells, especially human pluripotent cells, characterized in that the mammalian pluripotent stem cells, especially hPS cells, while undergoing differentiation into endoderm are exposed to a DNA demethylating agent.

The method for producing mammalian pluripotent stem cell-derived cells of the definitive endoderm, especially hPS cell-derived cells of the definitve endoderm, may be described as comprising:

Culturing mammalian pluripotent stem cells, especially human pluripotent stem cells, under differentiation conditions to obtain cells of the definitive endoderm, and Exposing the differentiating mammalian pluripotent stem cells, especially human pluripotent stem cells, to a DNA demethylating agent.

The DNA demethylating agent employed in the method according to the invention may be any compound that interferes with DNA methyltransferase enzyme activity. Suitable DNA demethylating agents are ones of the nucleoside-analog type, such as cytidine analogues, e.g. 5-aza-2-deoxycytidine (decitabine), 5-azacytidine (azacitidine) or zebularine, and of the non-nucleoside type, such as procaine, RG108, S-5-adenosyl-L-homocysteine, Caffeic acid, Chlorogenic acid, Epogallocatechin gallate, Hydralazine hydrochloride, Procainamide hydrochloride or Psammaplin A.

Thus, the DNA demethylating agent employed in the methods of the invention may be one of the nucleoside-analogue type. Alternatively, the DNA demethylating agent employed in the methods of the invention may be one of the non-nucleoside type. The DNA demethylating agent employed in the method of the invention may also be a mixture of both types.

Non-limiting examples of DNA demethylating agents of the nucleoside-analog type which may be employed in the method of the present invention are 5-aza-2-deoxycytidine (decitabine), 5-azacytidine (azacitidine) and zebularine. Non-limiting examples of the non-nucleoside type are procaine, RG108, S-5-adenosyl-L-homocysteine, Caffeic acid, Chlorogenic acid, Epogallocatechin gallate, Hydralazine hydrochloride, Procainamide hydrochloride or Psammaplin A.

Accordingly, the DNA demethylating agent employed in the method of the invention may be one selected from the group consisting of: 5-aza-2-deoxycytidine (decitabine) 5-azacytidine (azacitidine), zebularine, procaine, RG108, S-5-adenosyl-L-homocysteine, Caffeic acid, Chlorogenic acid, Epogallocatechin gallate, Hydralazine hydrochloride, Procainamide hydrochloride, Psammaplin A, and combinations thereof.

The DNA demethylating agent employed in the method of the invention may be a cytidine analogue, such as e.g. 5-aza-2-deoxycytidine (decitabine), 5-azacytidine (azacitidine), zebularine, Pseudoisocytidine, 5-fluoro-2-deoxycytidine, 5,6-dihydro-5-azacytidine, 2'-deoxy-5,6-dihydro-5-azacytidine, 6-azacytidine, 2',2'-Difluoro-deoxycytidine (gemcitabine), or Cytosine-beta-D-arabinofurasonide.

The DNA demethylating agent employed in the method of the invention may thus be a cytidine analogue selected from the group consisting of 5-aza-2-deoxycytidine (decitabine), 5-azacytidine (azacitidine), 5-fluoro-2-deoxycytidine, 5,6-dihydro-5-azacytidine, 2'-deoxy-5,6-dihydro-5-azacytidine, 6-azacytidine and 2',2'-Difluoro-deoxycytidine (gemcitabine), The DNA demethylating agent employed in the method of the invention may thus be a cytidine analogue selected from the group consisting of 5-aza-2-deoxycytidine (decitabine) and 5-azacytidine (azacitidine), Alternatively, the DNA demethylating agent employed in the methods of the invention may be a cytidine analogue which is not 5-aza-2-deoxycytidine (decitabine) or 5-azacytidine (azacitidine). The DNA demethylating agent employed in the method of the invention may thus be a cytidine analogue selected from the group consisting of 5-aza-2-deoxycytidine (decitabine), 5-azacytidine (azacitidine), 5-fluoro-2-deoxycytidine, 5,6-dihydro-5-azacytidine, 2'-deoxy-5,6-dihydro-5-azacytidine, 6-azacytidine and 2',2'-Difluoro-deoxycytidine (gemcitabine).

The DNA demethylating agent employed in the method of the invention may thus be 5-aza-2-deoxycytidine. The DNA demethylating agent may also be 5-azacytidine. The DNA demethylating agent may also be zebularine. The DNA demethylating agent may also be Pseudoisocytidine. The DNA demethylating agent may also be 5-fluoro-2-deoxycytidine. The DNA demethylating agent may also be 5,6-dihydro-5-azacytidine. The DNA demethylating agent may also be 2'-deoxy-5,6-dihydro-5-azacytidine. The DNA demethylating agent may also be 6-azacytidine. The DNA demethylating agent may also be 2',2'-Difluoro-deoxycytidine (gemcitabine). The DNA demethylating agent may also be Cytosine-beta-D-arabinofurasonide. The DNA demethylating agent may also be procaine. The DNA demethylating agent may also be RG108. The DNA demethylating agent may also be S-5-adenosyl-L-homocysteine. The DNA demethylating agent may also be Caffeic acid. The DNA demethylating agent may also be Chlorogenic acid. The DNA demethylating agent may also be Epogallocatechin gallate.

The DNA demethylating agent may also be Hydralazine hydrochloride. The DNA demethylating agent may also be Procainamide hydrochloride. The DNA demethylating agent may also be Psammaplin A.

The differentiating hPS cells may not only be exposed to one DNA demethylating agent, but may also be exposure to one or more further DNA demethylating agents, such as to a combination of two, three, four, five, six or seven of those mentioned above.

The differentiating mammalian pluripotent stem cells, especially hPS cells, may, for instance, be exposed to two of the DNA demethylating agents mentioned above. The differentiating mammalian pluripotent stem cells, especially hPS cells, may thus be exposed to a combination of 5-azacytidine (azacitidine) and 5-aza-2-deoxycytidine (decitabine) or to a combination of 5-azacytidine and zebularine. The differentiating mammalian pluripotent stem cells, especially hPS cells, may thus be exposed to a combination of 5-azacytidine (azacitidine) and 5,6-dihydro-5-azacytidine. The differentiating mammalian pluripotent stem cells, especially hPS cells, may thus be exposed to a combination of 5-aza-2-deoxycytidine (decitabine) and 5,6-dihydro-5-azacytidine. The differentiating mammalian pluripotent stem cells, especially hPS cells, may thus be exposed to a combination of 5-azacytidine (azacitidine) and 2'-deoxy-5,6-dihydro-5-azacytidine. The differentiating mammalian pluripotent stem cells, especially hPS cells, may thus be exposed to a combination of 5-aza-2-deoxycytidine (decitabine) and 2'-deoxy-5,6-dihydro-5-azacytidine. The differentiating mammalian pluripotent stem cells, especially hPS cells, may thus be exposed to a combination of 5-azacytidine (azacitidine) and 6-azacytidine. The differentiating mammalian pluripotent stem cells, especially hPS cells, may thus be exposed to a combination of 5-aza-2-deoxycytidine (decitabine) and 6-azacytidine. The differentiating mammalian pluripotent stem cells, especially hPS cells, may thus be exposed to a combination of 5-azacytidine (azacitidine) and 2',2'-Difluoro-deoxycytidine (gemcitabine). The differentiating mammalian pluripotent stem cells, especially hPS cells, may thus be exposed to a combination of 5-aza-2-deoxycytidine (decitabine) and 2',2'-Difluoro-deoxycytidine (gemcitabine).

The differentiating mammalian pluripotent stem cells, especially hPS cells, may also be exposed to a combination of a DNA demethylating agent of the nucleoside-analog type and a DNA demethylating agent of the non-nucleoside type, such as a combination of 5-aza-2-deoxycytidine and one of procaine, RG108, S-5-adenosyl-L-homocysteine, Caffeic acid, Chlorogenic acid, Epogallocatechin gallate, Hydralazine hydrochloride, Procainamide hydrochloride and Psammaplin A. The differentiating mammalian pluripotent stem cells, especially hPS cells, may also be exposed to three of the DNA demethylating agents mentioned above. The differentiating mammalian pluripotent stem cells, especially hPS cells may thus be exposed to a combination of 5-azacytidine (azacitidine), 5-aza-2-deoxycytidine (decitabine) and zebularine.

The differentiating mammalian pluripotent stem cells, especially hPS cells, may generally be exposed to the DNA demethylating agent at a concentration in the range of about 1 nM to about 10 μM, such as in the range of about 1 nM to about 5 μM The differentiating mammalian pluripotent stem cells, especially hPS cells, may, for instance, be exposed to the DNA demethylating agent at a concentration in the range of about 1 nM to about 1 μM. The differentiating mammalian pluripotent stem cells, especially hPS cells, may also be exposed to the DNA demethylating agent at a concentration in the range of about 1 nM to about 500 nM. The differentiating mammalian pluripotent stem cells, especially hPS cells, may also be exposed to the DNA demethylating agent at a concentration in the range of about 1 nM to about 250 nM. The differentiating mammalian pluripotent stem cells, especially hPS cells, may also be exposed to the DNA demethylating agent at a concentration in the range of about 1 nM to about 100 nM. The differentiating mammalian pluripotent stem cells, especially hPS cells, may thus be exposed to the DNA demethylating agent at a concentration in the range of about 1 nM to about 50 nM. The differentiating mammalian pluripotent stem cells, especially hPS cells, may thus be exposed to the DNA demethylating agent at a concentration in the range of about 1 nM to about 25 nM. The differentiating mammalian pluripotent stem cells, especially hPS cells, may thus be exposed to the DNA demethylating agent at a concentration in the range of about 1 nM to about 15 nM. The differentiating mammalian pluripotent stem cells, especially hPS cells, may also be exposed to the DNA demethylating agent at a concentration in the range of about 1 nM to about 10 nM. The differentiating mammalian pluripotent stem cells, especially hPS cells, may also be exposed to the DNA demethylating agent at a concentration in the range of about 5 nM to about 500 nM. The differentiating mammalian pluripotent stem cells, especially hPS cells, may thus be exposed to the DNA demethylating agent at a concentration in the range of about 5 nM to about 250 nM. The differentiating mammalian pluripotent stem cells, especially hPS cells, may also be exposed to the DNA demethylating agent at a concentration in the range of about 5 nM to about 100 nM. The differentiating mammalian pluripotent stem cells, especially hPS cells, may also be exposed to the DNA demethylating agent at a concentration in the range of about 5 nM to about 50 nM. The differentiating mammalian pluripotent stem cells, especially hPS cells, may also be exposed to the DNA demethylating agent at a concentration in the range of about 5 nM to about 25 nM. The differentiating mammalian pluripotent stem cells, especially hPS cells, may also be exposed to the DNA demethylating agent at a concentration in the range of about 5 nM to about 15 nM, such as in the range of about 10 nM. The differentiating mammalian pluripotent stem cells, especially hPS cells, may also be exposed to the DNA demethylating agent at a concentration in the range of about 7.5 nM to about 250 nM. The differentiating mammalian pluripotent stem cells, especially hPS cells, may also be exposed to the DNA demethylating agent at a concentration in the range of about 7.5 nM to about 100 nM. The differentiating mammalian pluripotent stem cells, especially hPS cells, may also be exposed to the DNA demethylating agent at a concentration in the range of about 7.5 nM to about 50 nM. The differentiating mammalian pluripotent stem cells, especially hPS cells, may also be exposed to the DNA demethylating agent at a concentration in the range of about 7.5 nM to about 25 nM. The differentiating mammalian pluripotent stem cells, especially hPS cells, may also be exposed to the DNA demethylating agent at a concentration in the range of about 7.5 nM to about 12.5 nM.

In case that, for instance, 5-aza-2-deoxycytidine is employed as the DNA demethylating agent, the differentiating mammalian pluripotent stem cells, especially hPS cells, may be exposed to it at a concentration in the range of 1 nM to about 1 pM. The differentiating mammalian pluripotent stem cells, especially hPS cells, may thus be exposed to 5-aza-2-deoxycytidine at a concentration in the range of about 1 nM to about 500 nM. The differentiating mammalian pluripotent stem cells, especially hPS cells, may also be exposed to 5-aza-2-deoxycytidine at a concentration in the range of about 1 nM to about 250 nM. The differentiating mammalian pluripotent stem cells, especially hPS cells, may also be exposed to 5-aza-2-deoxycytidine at a concentration in the range of about 1 nM to about 100 nM. The differentiating mammalian pluripotent stem cells, especially hPS cells, may thus be exposed to 5-aza-2-deoxycytidine at a concentration in the range of about 1 nM to about 50 nM. The differentiating mammalian pluripotent stem cells, especially hPS cells, may thus be exposed to 5-aza-2-deoxycytidine at a concentration in the range of about 1 nM to about 25 nM. The differentiating mammalian pluripotent stem cells, especially hPS cells, may thus be exposed to 5-aza-2-deoxycytidine at a concentration in the range of about 1 nM to about 15 nM. The differentiating mammalian pluripotent stem cells, especially hPS cells, may also be exposed to 5-aza-2-deoxycytidine at a concentration in the range of about 1 nM to about 10 nM. The differentiating mammalian pluripotent stem cells, especially hPS cells, may also be exposed to 5-aza-2-deoxycytidine at a concentration in the range of about 5 nM to about 500 nM. The differentiating mammalian pluripotent stem cells, especially hPS cells, may thus be exposed to 5-aza-2-deoxycytidine at a concentration in the range of about 5 nM to about 250 nM. The differentiating mammalian pluripotent stem cells, especially hPS cells, may also be exposed to 5-aza-2-deoxycytidine at a concentration in the range of about 5 nM to about 100 nM. The differentiating mammalian pluripotent stem cells, especially hPS cells, may also be exposed to 5-aza-2-deoxycytidine at a concentration in the range of about 5 nM to about 50 nM. The differentiating mammalian pluripotent stem cells, especially hPS cells, may also be exposed to 5-aza-2-deoxycytidine at a concentration in the range of about 5 nM to about 25 nM. The differentiating mammalian pluripotent stem cells, especially hPS cells, may also be exposed to 5-aza-2-deoxycytidine at a concentration in the range of about 5 nM to about 15 nM, such as in the range of about 10 nM. The differentiating mammalian pluripotent stem cells, especially hPS cells, may also be exposed to 5-aza-2-deoxycytidine at a concentration in the range of about 7.5 nM to about 250 nM. The differentiating mammalian pluripotent stem cells, especially hPS cells, may also be exposed to 5-aza-2-deoxycytidine at a concentration in the range of about 7.5 nM to about 100 nM. The differentiating mammalian pluripotent stem cells, especially hPS cells, may also be exposed to 5-aza-2-deoxycytidine at a concentration in the range of about 7.5 nM to about 50 nM. The differentiating mammalian pluripotent stem cells, especially hPS cells, may also be exposed to 5-aza-2-deoxycytidine at a concentration in the range of about 7.5 nM to about 25 nM. The differentiating mammalian pluripotent stem cells, especially hPS cells, may also be exposed to 5-aza-2-deoxycytidine at a concentration in the range of about 7.5 nM to about 12.5 nM.

Similar concentrations may be used in case that 5-azacytidine or zebularine are employed as the DNA demethylating agent. Similar concentrations may also be used in case of other cytidine analogues, such as, e.g. Pseudoisocytidine, 5-fluoro-2-deoxycytidine, 5,6-dihydro-5-azacytidine, 2'-deoxy-5,6-dihydro-5-azacytidine, 6-azacytidine, 2',2'-Difluoro-deoxycytidine (gemcitabine), or Cytosine-beta-D-arabinofurasonide, in particular 5-fluoro-2-deoxycytidine, 5,6-dihydro-5-azacytidine, 2'-deoxy-5,6-dihydro-5-azacytidine, 6-azacytidine or 2',2'-Difluoro-deoxycytidine (gemcitabine).

The differentiating mammalian pluripotent stem cells, especially hPS cells, may be exposed to (or treated with) said agent at any stage between pluripotent stem cell stage and endodermal stage. Thus, the exposure to said DNA demethylating agent may take place during the differentiation of the mammalian pluripotent stem cells, especially hPS cells, into DE cells.

The differentiating mammalian pluripotent stem cells, especially hPS cells, are usually exposed to the DNA demethylating agent of the nucleoside-analog type (e.g. 5aza-2deoxycytidine, 5-azacytidine, zebularine) when they show greatest proliferative capacity as evidenced by cell doubling time, such as between days 2 and 7 of differentiation. Thus, the DNA demethylating agent may be added to the differentiation medium on day 2 of differentiation. The DNA demethylating agent may also be added to the differentiation medium on day 3 of differentiation. The DNA demethylating agent may also be added to the differentiation medium on day 4 of differentiation. The DNA demethylating agent may also be added to the differentiation medium on day 5 of differentiation. The DNA demethylating agent may also be added to the differentiation medium on day 6 of differentiation. DNA demethylation agents of the non-nucleoside type (e.g. procaine, RG108, S-5-adenosyl-L-homocysteine) can be added at any time in the differentiation protocol since they do not require cell proliferation to have an effect.

The treatment of differentiating mammalian pluripotent stem cells, especially hPS cells, with a DNA demethylating agent has surprisingly been found to lead to an improved morphology and improved yield of definitive endodermal cells. Moreover, treatment with a demethylating agent provides for more pure and homogenous endodermal cell populations (FIG. 1A-B). Moreover, treatment with a DNA demethylating agent also surprisingly leads to a significant down-regulation of expression of the stem cell marker Oct4 in endodermal cells (FIG. 1C and D) and to an improved protein and gene expression of the DE specific markers sox17, cxcr4 and hhex (FIG. 1D). It is believed to be the first time that such effects are shown for DNA demethylation and the application of growth factors involved in the differentiation of mammalian pluripotent stem cells, especially hPS cells, towards definitive endoderm. Without to be bound by theory, it is believed that the action of the involved growth factors at a genomic level is enhanced by the widespread absence of methylation.

The starting material in the present invention may be any type of mammalian pluripotent stem cells, such as mammalian embryonic stem cells or mammalian induced pluripotent stem cells.

The mammalian pluripotent stem cells employed in the present invention may, for instance, be human pluripotent stem cells, primate pluripotent stem cells, mouse pluripotent stem cells, rat pluripotent stem cells, canine pluripotent stem cells, feline pluripotent stem cells, procine pluripotent stem cells, bovine pluripotent stem cells or equine pluripotent stem cells.

Especially, the starting material in the present invention may be any type of human pluripotent stem cells, such as human embryonic stem (hES) cells or human induced pluripotent stem (hiPS) cells.

Accordingly, the human pluripotent stem cells which are used as starting material to obtain DE cells may be human embryonic stem cells. Various techniques for obtaining such hES cells are known to the skilled person. Preferably, however, the hES cells for use according to the invention are ones which have been derived (or obtained) without destruction of the human embryo, such as by employing the single blastomere removal technique described in e.g. Chung et al (2008), further described by Mercader et al. in Essential Stem Cell Methods (First Edition, 2009). Suitable hES cell lines for use are, for example, the cell lines SA167, SA181, SA461 (Cellartis AB, Göteborg, Sweden) which are listed in the NIH stem cell registry, the UK Stem Cell bank and the European hESC registry and are available on request. Other suitable cell lines for use are those established by Klimanskaya et al. (2006), such as cell lines MA01 and MA09, and Chung et al. (2008), such as cell lines MA126, MA127, MA128 and MA129, which all are listed with the International Stem Cell Registry (assigned to Advanced Cell Technology, Inc. Worcester, Mass., USA).

Alternatively, the human pluripotent stem cells which may be used as starting material to obtain the endodermal and/or hepatic progenitor cells may be human induced pluripotent stem cells. Various techniques for obtaining such hiPS cells have been described in the scientific literature, and are thus known to the skilled person [see, e.g., Takahashi et al. (2007); Zhou et al. (2009); Yu and Thomson in Essentials of Stem Cell Biology ($2^{nd}$ Edition].

The starting material in the present invention may be any type of mammalian pluripotent stem cells, such as mammalian embryonic stem cells or mammalian induced pluripotent stem cells, which mammalian pluripotent stem cells are not human pluripotent stem cells.

Suitable conditions for differentiating mammalian pluripotent stem cells, especially hPS cells, into DE cells are known (see, e.g., Hay 2008, Brolen 2010 and Duan 2010). WO 2009/013254 A1, for example, describes suitable protocols to obtain cells of the definitive endoderm from hPS cells (Embodiments 1 to 4).

Generally, in order to obtain endodermal cells, mammalian pluripotent stem cells, especially hPS cells, are cultured in a differentiation medium comprising activin, such as activin A or B. The differentiation medium may further include a histone deacetylase (HDAC) inhibitor, such as Sodium Butyrate (NaB), Phenylbutyrate (PB), valproate, trichostatin A, Entinostat or Panobinstat. The differentiation medium may further comprise one or more growth factors, such as FGF1, FGF2 and FGF4, and/or serum, such as FBS or FCS. The differentiation medium may comprise a GSK3-inhibitor, such as, e.g., CHIR99021, or an activator of Wnt signalling, such as Wnt3A. The differentiation medium may further comprise a PI3K (Phosphoinositide 3-kinase) inhibitor, such as LY294002.

The concentration of activin is usually in the range of about 50 to about 150 ng/ml, such as about 80 to about 120 ng/ml. Activin may, for example, be present in the differentiation medium at a concentration of about 50 ng/ml or about 100 ng/ml. The concentration of the HDAC inhibitor is usually in the range of about 0.5 to about 2 mM. The HDAC inhibitor may, for example, be present in the differentiation medium at a concentration of about 0.5 mM or about 1 mM. The concentration of the one or more growth factors may vary depending on the particular compound used. The concentration of FGF2, for example, is usually in the range of about 2 to about 50 ng/ml, such as about 2 to about 10 ng/ml. FGF2 may, for example, be present in the differentiation medium at a concentration of about 4 or about 5 ng/ml. The concentration of FGF1, for example, is usually in the range of about 50 to about 200 ng/ml, such as about 80 to about 120 ng/ml. FGF1 may, for example, be present in the differentiation medium at a concentration of about 100 ng/ml. The concentration of FGF4, for example, is usually in the range of about 20 to about 40 ng/ml. FGF4 may, for example, be present in the differentiation medium at a concentration of about 30 ng/ml. The concentration of serum, if present, is usually in the range of about 0.1 to about 2% v/v, such as about 0.1 to about 0,5%, about 0,2 to about 1.5% v/v, about 0.2 to about 1% v/v, about 0.5 to 1% v/v or about 0.5 to about 1.5% v/v. Serum may, for example, be present in the differentiation medium at a concentration of about 0,2% v/v, about 0.5% v/v or about 1% v/v. The concentration of the GSK3 inhibitor, if present, is usually in the range of about 0.1 to about 10 μM, such as about 0.05 to about 5 μM. The concentration of the activator of Wnt signalling, if present, is usually in the range of about 0.05 to about 10 ng/ml, such as about 0.5 to about 5 μM. The concentration of the P13K inhibitor, for example, is usually in the range of about 0.1 to 10 μM, such as about 1 to 5 μM.

The differentiation medium may further comprise other supplements such as PEST and/or GlutaMAX. The differentiation medium may also further comprise a ROCK inhibitor. The concentration of PEST is usually in the range of about 0.1 to about 0.5% v/v, such as about 0.1 to about 0,25% v/v. The concentration of GlutaMAX is usually in the range of about 0.5 to about 1.5% v/v, such as about 0.75 to 1.25% v/v, e.g. about 1% v/v. The differentiation medium may also further comprise a ROCK inhibitor. The concentration of the ROCK inhibitor is usually in the range of about 1 to about 10 μM, such as about 2.5 to about 7.5 μM, e.g., about 5 μM.

The culture medium forming the basis for the differentiation medium may be any culture medium suitable for culturing mammalian pluripotent stem cells, especially hPS cells, such as RPMI 1640 or advanced RPMI 1640 medium, Dulbecco's Modified Eagle Medium (DMEM), HCM medium, HBM medium or Williams E based medium. Thus, the differentiation medium may be RPMI 1640 or advanced RPMI 1640 medium comprising or supplemented with the above-mentioned components. Alternatively, the differentiation medium may be DMEM comprising or supplemented with the above-mentioned components. The differentiation medium may thus also be HCM medium comprising or supplemented with the above-mentioned components. The differentiation medium may thus also be HBM medium comprising or supplemented with the above-mentioned components. The differentiation medium may thus also be Williams E based medium comprising or supplemented with the above-mentioned components.

For endodermal differentiation, mammalian pluripotent stem cells, especially hPS cells, are normally cultured for up to 10 days in an activin containing differentiation medium as described above. The mammalian pluripotent stem cells, especially hPS cells, may, for example, be cultured in said differentiation medium for about 4 to about 10 days, such as for about 4 to about 9 days, for about 4 to about 7 days or for about 7 to about 9 days.

Basic, non-limiting culture conditions for obtaining cells of the definitive endoderm from mammalian pluripotent stem cells, especially hPS cells, are provided in Example 2 herein.

Further, the endodermal cells of the present invention may be obtained under xeno-free conditions. As such, the starting material employed in the method of the invention may thus be xeno-free, such as xeno-free hPS cells or cell lines which have been obtained or established under animal-free conditions. Moreover, throughout the method of the invention cells may be cultured completely under xeno-free conditions, giving rise to truly xeno-free endodermal cells. Such cells or cell line could be distinguished from a non-xeno free composition by the presence in non-xeno free cells of the non-human sialic acid Neu5Gc or other non-human markers (Martin et al 2005).

As a result of the methods of the present invention, endodermal cells, e.g., DE cells, are obtained with improved features compared to currently available state of the art methods.

The populations of definitive endodermal cells or cell compositions obtained in accordance to the invention show an improved lower expression of stem cell markers like Oct4, compared to cell populations or cell compositions obtained without treatment with a DNA demethylating agent. Further, the populations of definitive endodermal cells or cell compositions show an increased gene expression of a number of markers characteristic for definitive endodermal cells, notably sox17, cxcr4 and hhex. Moreover, the obtained populations of definitive endodermal cells or cell compositions are more pure and homogenous compared to ones obtained without treatment with a DNA demethylating agent.

The cell composition(s) of the invention may further be characterized in that at least 70% such as e.g. 75%, 80%, 90% or 95% of the cells are endodermal cells of the present invention.

Once obtained, the endodermal cell(s) or cell composition(s) of the invention may further be used to produce cells or tissue of the intestine, pancreas, liver and/or lung. The endodermal cell(s) or cell composition(s) of the invention, may, for instance, be used to produce hepatic progenitor cells or fully matured hepatocyte-like cells, including hepatic tissue. The endodermal cell(s) or cell composition(s) of the invention may also be used to produce pancreatic precursor cells or fully matured pancreatic cells, such as pancreatic stellate cells or Langerhans cells, or pancreatic tissue.

The endodermal cell(s) or cell composition(s) of the invention may also be further used in pharmaceutical and toxicological screening, such as drug discovery processes or toxicity testing.

The invention also provides kits. Such kits are particularly useful in carrying out the methods of the invention, i.e. for producing cells of the definitive endoderm from mammalian pluripotent stem cells, such as human pluripotent stem cells. A kit according to the invention comprises at least one DNA demethylating agent.

As noted above, it is understood that the details given herein with respect to the components employed in the methods of the invention also apply to the components comprised by the kits of the invention.

Hence, the at least one DNA demethylating agent comprised by a kit of the invention may, for instance, be a cytidine analogue, such as e.g. 5-aza-2-deoxycytidine (decitabine), 5-azacytidine (azacitidine), zebularine, Pseudoisocytidine, 5-fluoro-2-deoxycytidine, 5,6-dihydro-5-azacytidine, 2'-deoxy-5,6-dihydro-5-azacytidine, 6-azacytidine, 2',2'-Difluoro-deoxycytidine (gemcitabine), or Cytosine-beta-D-arabinofurasonide.

The at least one DNA demethylating agent comprised by a kit of the invention may, for instance, be a cytidine analogue selected from the group consisting of 5-aza-2-deoxycytidine (decitabine), 5-azacytidine (azacitidine), 5-fluoro-2-deoxycytidine, 5,6-dihydro-5-azacytidine, 2'-deoxy-5,6-dihydro-5-azacytidine, 6-azacytidine and 2',2'-Difluoro-deoxycytidine (gemcitabine), The at least one DNA demethylating agent comprised by a kit of the invention may, for instance, be 5-aza-2-deoxycytidine (decitabine) or 5-azacytidine (azacitidine), Alternatively, the at least one DNA demethylating agent comprised by a kit of the invention may, for instance, be a cytidine analogue which is not 5-aza-2-deoxycytidine (decitabine) or 5-azacytidine (azacitidine), A kit of the invention may further comprise mammalian pluripotent stem cells, especially human pluripotent stem cells. Hence, a kit of the invention may comprise mammalian embryonic stem cells, especially human embryonic stem cells, and/or mammalian induced pluripotent stem cells, especially human induced pluripotent stem cells. The mammalian pluripotent stem cells, especially human pluripotent stem cells, may suitably be provided as a cell suspension, and may be provided in a frozen state.

A kit of the invention may further comprise activin, such as activin A or B.

A kit of the invention may further comprise one or more growth factors, such as FGF1, FGF2 and FGF4, and/or serum, such as FBS or FCS.

A kit of the invention may comprise 5-aza-2-deoxycytidine (decitabine) or 5-azacytidine (azacitidine) and mammalian pluripotent stem cells, especially human pluripotent stem cells, such as human embryonic stem cells or human induced pluripotent stem cells.

A kit of the invention may comprise 5-aza-2-deoxycytidine (decitabine) or 5-azacytidine (azacitidine), activin, such activin A or B, and mammalian pluripotent stem cells, especially human pluripotent stem cells, such as human embryonic stem cells or human induced pluripotent stem cells.

The components of a kit of the invention may be provided in the same or separate containers. For instance, the at least one DNA demethylating agent and activin may be provided in the same container. If mammalian pluripotent stem cells, especially human pluripotent stem cells, are comprised by a kit, the mammalian pluripotent stem cells, such as human pluripotent stem cells are generally provide in a container which is different from the container(s) containing the other components.

The invention also provides compositions. Such compositions are particularly useful for producing cells of the definitive endoderm from mammalian pluripotent stem cells, especially human pluripotent stem cells. A composition of the invention comprises at least one DNA demethylating agent and activin, such as activin A or B.

As noted above, it is understood that the details given herein with respect to the components employed in the methods of the invention also apply to the components comprised by the compositions of the invention.

Hence, the at least one DNA demethylating agent comprised by a composition of the invention may, for instance, be a cytidine analogue, such as e.g. 5-aza-2-deoxycytidine (decitabine), 5-azacytidine (azacitidine), zebularine, Pseudoisocytidine, 5-fluoro-2-deoxycytidine, 5,6-dihydro-5-azacytidine, 2'-deoxy-5,6-dihydro-5-azacytidine, 6-azacytidine, 2',2'-Difluoro-deoxycytidine (gemcitabine), or Cytosine-beta-D-arabinofurasonide.

The at least one DNA demethylating agent comprised by a composition of the invention may, for instance, be a cytidine analogue selected from the group consisting of 5-aza-2-deoxycytidine (decitabine), 5-azacytidine (azacitidine), 5-fluoro-2-deoxycytidine, 5,6-dihydro-5-azacytidine, 2'-deoxy-5,6-dihydro-5-azacytidine, 6-azacytidine and 2',2'-Difluoro-deoxycytidine (gemcitabine), The at least one DNA demethylating agent comprised by a composition of the invention may, for instance, be 5-aza-2-deoxycytidine (decitabine) or 5-azacytidine (azacitidine). Alternatively, the at least one DNA demethylating agent comprised by a composition of the invention may, for instance, be a cytidine analogue which is not 5-aza-2-deoxycytidine (decitabine) or 5-azacytidine (azacitidine), A composition of the invention may further comprise one or more growth factors, such as FGF1, FGF2 and FGF4, and/or serum, such as FBS or FCS.

Accordingly, a composition of the invention may comprise 5-aza-2-deoxycytidine (decitabine) and activin, such as activin A or B.

A composition of the invention may comprise 5-azacytidine (azacitidine) and activin, such as activin A or B.

DEFINITIONS

As used herein, "pluripotent" or "pluripotency" refers to the potential to form all types of specialized cells of the three germ layers (endoderm, mesoderm, and ectoderm); and is to be distinguished from "totipotent" or "totipotency", that is the ability to form a complete embryo capable of giving rise to offsprings.

As used herein, "human pluripotent stem cells" (hPS) refers to human cells that have the capacity, under appropriate conditions, to self-renew as well as the ability to form any type of specialized cells of the three germ layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human embryonic stem (hES) cells, (see, e.g., Thomson et al. (1998), Heins et. al. (2004), as well as induced pluripotent stem cells [see, e.g. Takahashi et al., (2007); Zhou et al. (2009); Yu and Thomson in Essentials of Stem Cell Biology ($2^{nd}$ Edition]. The various methods described herein may utilise hPS cells from a variety of sources. For example, hPS cells suitable for use may have been obtained from developing embryos by use of a non-destructive technique such as by employing the single blastomere removal technique described in e.g. Chung et al (2008), further described by Mercader et al. in Essential Stem Cell Methods (First Edition, 2009). Additionally or alternatively, suitable hPS cells may be obtained from established cell lines or may be adult stem cells.

As used herein "hiPS cells" refers to human induced pluripotent stem cells. hiPS cells are a type of pluripotent stem cells derived from non-pluripotent cells—typically adult somatic cells—by induction of the expression of genes associated with pluripotency, such as SSEA-3, SSEA-4, TRA-1-60, TRA-1-81, Oct-4, Sox2, Nanog and Lin28.

As used herein, "definitive endoderm (DE)", "cells of the definitive endoderm" and "definitive endodermal cells (DE cells)" refers to cells cells exhibiting protein and/or gene expression as well as morphology typical to cells of the definitive endoderm or a composition comprising a significant number of cells resembling the cells of the definitive endoderm. The definitive endoderm is the germ cell layer which gives rise to cells of the intestine, pancreas, liver and lung. DE cells may generally be characterized, and thus identified, by a positive gene and protein expression of the endodermal markers FOXA2, CXCR4, H HEX, SOX17, GATA4 and GATA6. The two markers SOX17 and CXCR4 are specific for DE and not detected in hPS cells. Lastly, DE cells do not exhibit gene and protein expression of the undifferentiated cell markers Oct4, SSEA-3, SSEA-4, TRA-1-60, TRA-1-81, but can show low Nanog expression.

As used herein, "hepatic progenitors" or "hepatic progenitor cells" refers to cells which have entered the hepatic cell path and give rise to hepatocyte. "Hepatic progenitors" are thus distinguished from "endodermal cells" in that they have lost the potential to develop into cells of the intestine, pancreas and lung. "Hepatic progenitors" may generally be characterized, and thus identified, by a positive gene and protein expression of the early hepatic markers EpCAM, c-Met (HGF-receptor), AFP, CK19, HNF6, C/EBPα and β. They do not exhibit gene and protein expression of the DE-markers CXCR4 and SOX17. Lastly, "hepatic progenitors" do not exhibit gene and protein expression of the undifferentiated cell markers Oct4, SSEA-3, SSEA-4, TRA-1-60 and TRA-1-81 nor the mature hepatic markers CYP1A2, CYP2C9, CYP19, CYP3A4, CYP2B6 and PXR.

As used herein, "hepatocyte" or "hepatocyte-like cells" refers to fully differentiated hepatic cells. "Hepatocytes" or "hepatocytes-like cells" may generally be described, and thus identified, by a positive gene and protein expression of the mature hepatic markers CYP1A2, CYP3A4, CYP2C9, CYP2C19, CYP2B6, GSTA1-1, OATP-2, NTCP, Albumin, PXR, CAR, and HNF4a (isoforms 1+2) among others. Further, "hepatocytes" or "hepatocyte-like cells do not exhibit gene and protein expression of the undifferentiated cell markers Oct4, SSEA-3, SSEA-4, TRA-1-60 and TRA-1-81. Compared to DE cells, "hepatocytes" or "hepatocyte-like cells do not exhibit gene and protein expression of the DE cell markers SOX17 and CXCR4. Compared to "hepatic progenitors", "hepatocytes" or "hepatocyte-like cells do not exhibit gene and protein expression of the hepatic progenitor markers Cytokeratin 19 and AFP.

As meant herein, a gene or protein shall be interpreted as being "expressed", if in an experiment measuring the expression level of said gene or protein, the determined expression level is higher than three times the standard deviation of the determination, wherein the expression level and the standard deviation are determined in 10 separate determinations of the expression level. The determination of the expression level in the 10 separate determinations is preferably corrected for background-signal.

As used herein HDAC inhibitors refers to Histone deacetylase inhibitors, such as Sodium Butyrate ("NaB"), Phenyl Butyrate ("PB"), Trichostatin A and Valproic Acid ("VA").

As used herein, "GSK inhibitor" refers to a compound which inhibits a Glycogen synthase kinase (especially GSK3, including GSK3alpha or GSK3beta).

As used herein, "activator of Wnt signalling" refers to a compound which activates Wnt signalling.

As used herein, a DNA demethylating agent is intended to mean a compound that interferes with DNA methyltransferase enzyme activity, such as nucleoside analogues, like cytidine analogs, notably 5-aza-2-deoxycytidine (decitabine), 5-azacytidine (azacitidine), and zebularine, and non-nucleoside types, such as RG108, S-5-Adenosyl-L-homocysteine, and procaine.

As used herein, the term "FGF" means fibroblast growth factor, preferably of human and/or recombinant origin, and subtypes belonging thereto are e.g. "bFGF" (means basic fibroblast growth factor, sometimes also referred to as FGF2) and FGF4. "aFGF" means acidic fibroblast growth factor (sometimes also referred to as FGF1).

As used herein, the term "Activin" is intended to mean a TGF-beta family member that exhibits a wide range of biological activities including regulation of cellular proliferation and differentiation such as "Activin A" or "Activin B". Activin belongs to the common TGF-beta superfamily of ligands.

As used herein, the term "ROCK inhibitor" is intended to mean an inhibitor of ROCK Rho-associated protein kinase activity As used herein the term "xeno-free" is intended to mean complete circumvention of direct or in-direct exposure to non-human animal components.

BRIEF DESCRIPTION OF THE DRAWINGS

FIG. 1A-1. Morphology of hESC-derived definitive endodermal cells (derived with basic protocol A) without a 5-aza-deoxycytidine treatment during the pre-endodermal phase (day 0-7 of the protocol).

FIG. 1A-2. Morphology of hESC-derived definitive endodermal cells (derived with basic protocol A) with a 5-aza-deoxycytidine treatment during the pre-endodermal phase (day 0-7 of the protocol).

FIG. 1B-1. Morphology of hiPSC-derived definitive endodermal cells (derived with basic protocol A) without a 5-aza-deoxycytidine treatment during the pre-endodermal phase (day 0-7 of the protocol).

FIG. 1B-2. Morphology of hiPSC-derived definitive endodermal cells (derived with basic protocol A) with a 5-aza-deoxycytidine treatment during the pre-endodermal phase (day 0-7 of the protocol).

FIG. 1C-1. Oct4-immunstaining and DAPI nuclear staining of hiPSC-derived definitive endodermal cells (derived with basic protocol A) without a 5-aza-deoxycytidine treatment during the pre-endodermal phase (day 0-7 of the protocol).

FIG. 1C-2. Oct4-immunstaining and DAPI nuclear staining of hiPSC-derived definitive endodermal cells (derived with basic protocol D) with a 5-aza-deoxycytidine treatment during the pre-endodermal phase (day 0-7 of the protocol).

FIG. 1D-1. mRNA expression of stem cell marker Oct4 in hESC- and hiPSC-derived definitive endodermal cells (derived with basic protocol A) with and without a 5-aza-deoxycytidine treatment during the pre-endodermal phase (day 0-7 of the protocol).

FIG. 1D-2. mRNA expression of stem cell marker Nanog in hESC- and hiPSC-derived definitive endodermal cells (derived with basic protocol A) with and without a 5-aza-deoxycytidine treatment during the pre-endodermal phase (day 0-7 of the protocol).

FIG. 1D-3. mRNA expression of DE marker Sox17 in hESC- and hiPSC-derived definitive endodermal cells (derived with basic protocol A) with and without a 5-aza-deoxycytidine treatment during the pre-endodermal phase (day 0-7 of the protocol).

FIG. 1D-4. mRNA expression of DE marker Cxcr4 in hESC- and hiPSC-derived definitive endodermal cells (derived with basic protocol A) with and without a 5-aza-deoxycytidine treatment during the pre-endodermal phase (day 0-7 of the protocol).

FIG. 1D-5. mRNA expression of DE marker FoxA2 in hESC- and hiPSC-derived definitive endodermal cells (derived with basic protocol A) with and without a 5-aza-deoxycytidine treatment during the pre-endodermal phase (day 0-7 of the protocol).

FIG. 1D-6. mRNA expression of DE marker hHEX in hESC- and hiPSC-derived definitive endodermal cells (derived with basic protocol A) with and without a 5-aza-deoxycytidine treatment during the pre-endodermal phase (day 0-7 of the protocol).

FIG. 1D-7. mRNA expression of extraembryonic marker Sox7 in hESC- and hiPSC-derived definitive endodermal cells (derived with basic protocol A) with and without a 5-aza-deoxycytidine treatment during the pre-endodermal phase (day 0-7 of the protocol).

EXAMPLES

Figures 1, 1D:
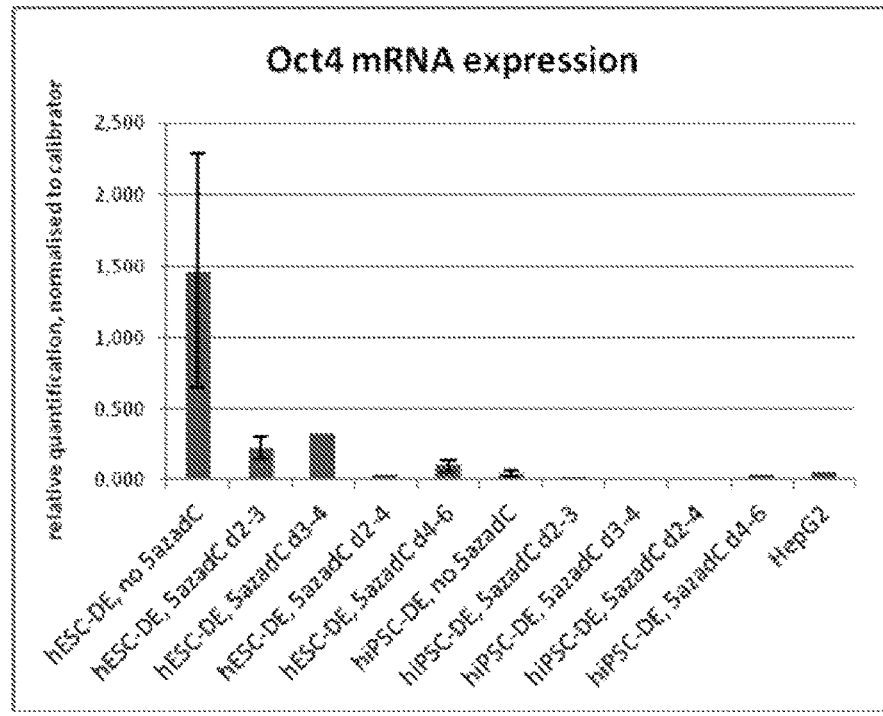

Examples of general culturing and passaging techniques are disclosed in applications WO2004/099394, WO2003/055992, WO/2007/042225, WO2007/140968 and WO2011116930.

As laid out in the following examples, the starting material are human pluripotent stem cells, in particular human embryonic stem cells and human induced pluripotent stem cells.

Example 1

Maintenance of hPS Cell Types

All hPS cells (as defined above) can be used as staring material for this invention. For the examples below in particular definitive endoderm was derived in vitro from undifferentiated human embryonic stem cells (hESC) established on mEF feeder cells (Heins et al 2004) and maintained under feeder-free conditions. The cell lines used for this experiment could be, but are not limited to the hES cell lines SA167, SA181, SA461 (Cellartis A B, Göteborg, Sweden) and they can be propagated as described by Heins et al. 2004. These cell lines are listed in the NIH stem cell registry, the UK Stem Cell bank and the European hESC registry and are available on request.

Along with hPS obtained from hESC, hiPS (human induced pluripotent stem) cells have also been used for the derivation of hepatocytes for the examples of this invention.

The hiPSC line used in this invention are derived as followed: Human dermal fibroblasts (CRL2429, ATCC) were maintained in DMEM supplemented with 10% fetal bovine serum, 1× glutamax, 5 U/ml penicillin and 5 μg/ml streptomycin at 37° C. in a humidified atmosphere of 5% $CO_2$ in air. Fibroblasts were tranduced with recombinant lentiviruses encoding mouse Oct4, Sox2, Klf4 and c-myc and cultured for 5 days. The transduced cells were then dispersed with trypsin and seeded onto mitomycin C treated human dermal fibroblast feeder cells at a density of $5 \times 10^3$ cells/cm$^2$ in their normal growth medium. After 24 hours the medium was replaced with knockout DMEM supplemented with 20% knockout serum replacement, 1× non-essential amino acids, 1× glutamax, 5 U/ml penicillin, 5 μg/ml streptomycin, 100 μM 2-mercaptoethanol and 30 ng/ml bFGF at 37° C. in a humidified atmosphere of 5% $CO_2$ in air. Half of the volume of medium was replaced every day and colonies of iPS cells emerged after approximately 30 days. iPS colonies were picked, expanded in DEF-CS™, and cell banks prepared. The banked cells were then characterised to check for the expression of endogenous Oct4, Sox2, Klf4 and c-Myc, silencing of transgenes, potential to differentiate into cell types representative of all three germ layers in vitro, and to confirm their authenticity by STR profiling and comparison with the parental fibroblast cell line (ATCC). Alternatively to reprogramming using lentivirus, hiPSC lines can also be reprogrammed using retrovirus, Sendai virus, adenovirus, episomal plasmid vectors, proteins and mRNAs or other techniques. Other suitable cell lines for use are those established by Chung et al. (2008), such as cell lines MA126, MA127, MA128 and MA129 (Advanced Cell Technology, Inc. Worcester, Mass., USA), which all are listed with the International stem cell registry. These cell lines have been derived (or obtained) without destruction of the human embryo by employing a single blastomere removal technique.

Example 2

Differentiation of hPS Cell Types to Produce Hepatocyte-like Cells Hepatocyte-like Cells may be derived from hPS cells by employing the following Exemplary Basic Protocols A and B Protocol A:
Undifferentiated hPS cells are dissociated and seeded directly in freshly prepared day 0-medium. The different mediums were prepared freshly and added day 0, 1, 2, 3, 4, 5, 7. The pre-treatment medium is available from Cellectis AB (Arvid Wallgrens Backe 20, 41356 Gothenburg, Sweden).
Day 0
Pre-treatment medium
3 μM CHIR99021
5 μM ROCK inhibitor
Day 1
Pre-treatment medium
3 μM CHIR99021
Day 2
RPMI 1640 (+0.1% PEST +1% Glutamax)
1×B27
50 ng/ml Activin A
3 μM CHIR99021
5 μM LY294002
Day 3
RPMI 1640 (+0.1% PEST +1% Glutamax)
1×B27
50 ng/ml Activin A
5 μM LY294002
Day 4-7
RPMI 1640 (+0.1% PEST+1% Glutamax)
1×B27
50 ng/ml Activin A On day 7 the cells are passaged. The cells are incubated for 3-7 minutes with TrypLE Select at 37° C., the same volume of VitroHES is added and the cell suspension is centrifuged at 200-300 g, 5-6 min. Thereafter, the cells are replated onto a Fibronectin-based coating at a cell density of 50 000-350 000 cells/cm$^2$ such as e.g. 100 000-300 000 cells/cm$^2$, preferably 150 000 cells/cm$^2$.

Protocol B:
Undifferentiated hPS cells are dissociated and seeded directly in freshly prepared day 0-medium. The different mediums were prepared freshly and added day 0, 1, 2, 3, 4, 5, 7. The pre-treatment medium is available from Cellectis AB (Arvid Wallgrens Backe 20, 41356 Gothenburg, Sweden).
Day 0
Pre-treatment medium
3 μM CHIR99021
5 μM ROCK inhibitor
Day 1
RPMI 1640 (+0.1% PEST+1% Glutamax)
1×B27
50 ng/ml Activin A
3 μM CHIR99021
5 μM LY294002
Day 2
RPMI 1640 (+0.1% PEST+1% Glutamax)
1×B27
50 ng/ml Activin A
5 μM LY294002
Day 3-7
RPMI 1640 (+0.1% PEST+1% Glutamax)
1×B27
50 ng/ml Activin A
For passage d7 see Protocol A.

Example 3

Validation of Improved Definitive Endoderm Phenotype in hESC and Hips Cells Treated with DNA Demethylation Procedure:
Following the basic protocol A (both for hESC- and hiPSC-derived definitive endoderm), cells were treated with 10 nM 5-aza-2-deoxycytidine at different time points and for different durations during the pre-endodermal phase, e.g. on day 2-3, 2-4, 3-4 and 4-6 of the protocol (hESC-DE: no 5azadC n=4, 5azadC d2-3 n=4, d3-4 n=1, d2-4 n=1, d4-6 n=1; hiPSC-DE: no 5azadC n=5, 5azadC d2-3 n=5, d3-4 n=2, d2-4 n=1, d4-6 n=1; with n being the number of individual experiments).

For analysis of mRNA expression, hESC- and hiPSC-derived DE-cells were harvested on day 7 of the protocol and gene expression was analysed using qRT-PCR, normalised to the house-keeping gene CREBBP, and the results presented as relative quantification normalised to a calibrator.

Figures 1, 1D, 2:
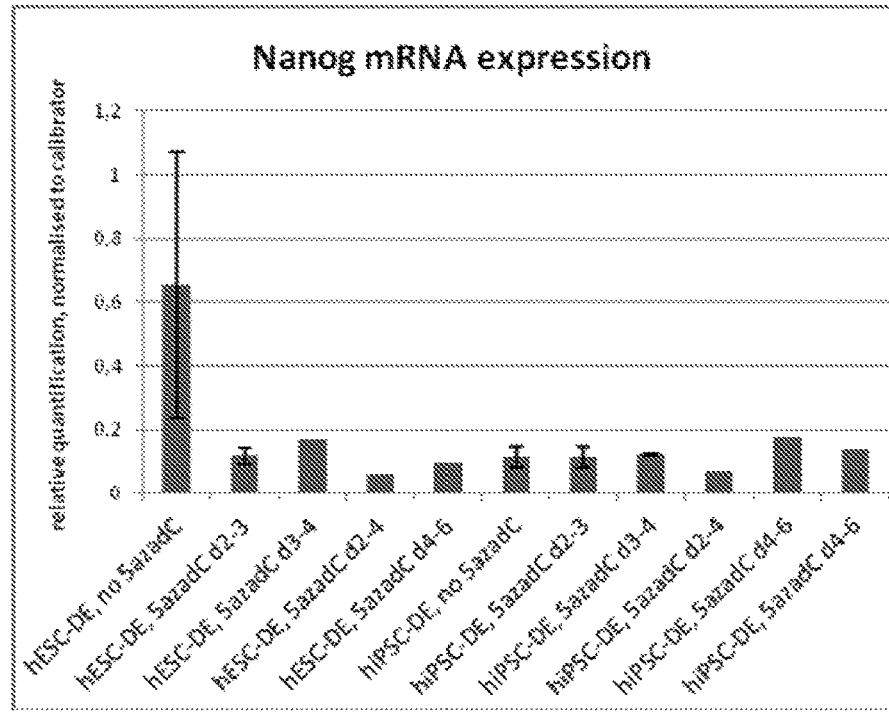
Figures 1, 1D, 2, 3:
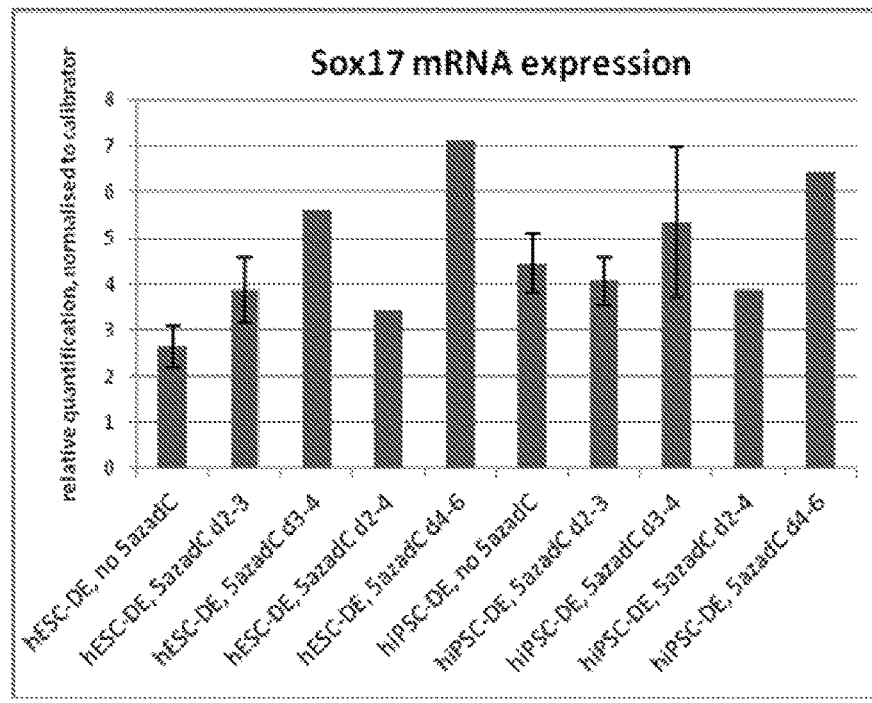
Figures 1, 1D, 2, 3, 4:
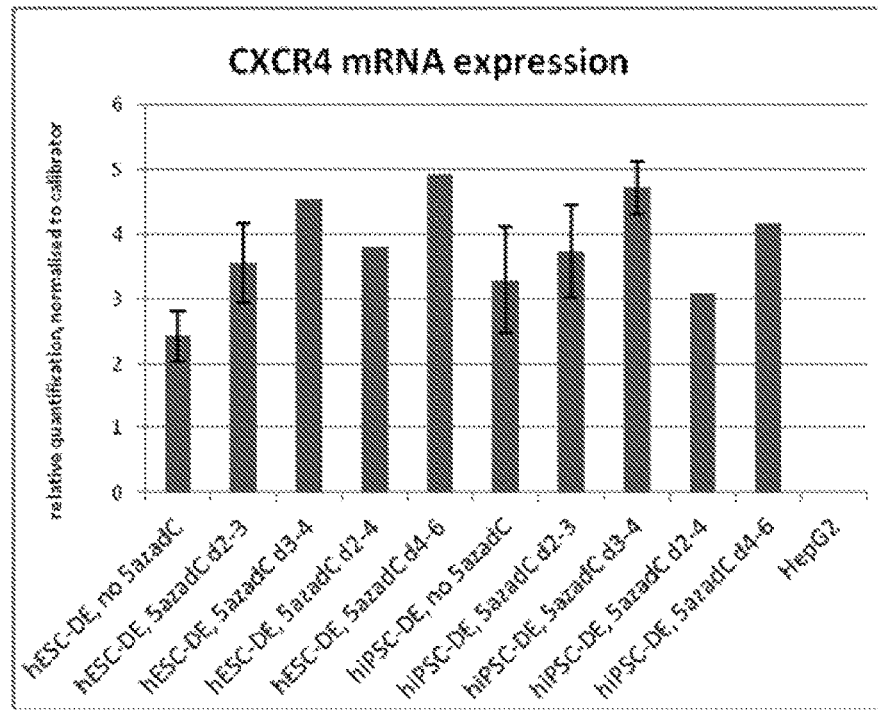
Figures 1, 1D, 2, 3, 4, 5:
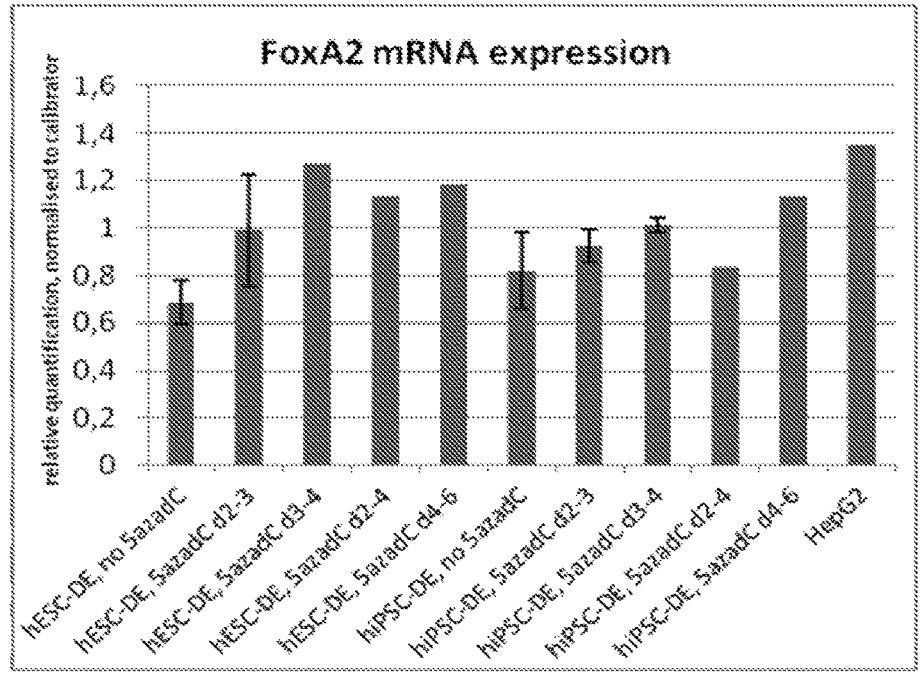
Figures 1, 1D, 2, 3, 4, 5, 6:
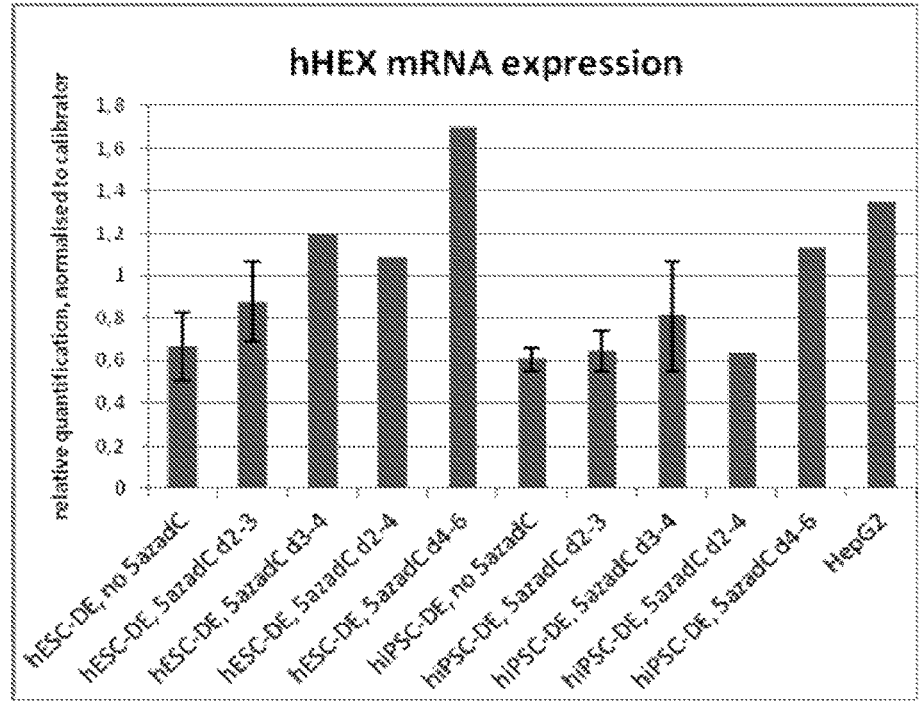
Figures 1, 1D, 2, 3, 4, 5, 6, 7:
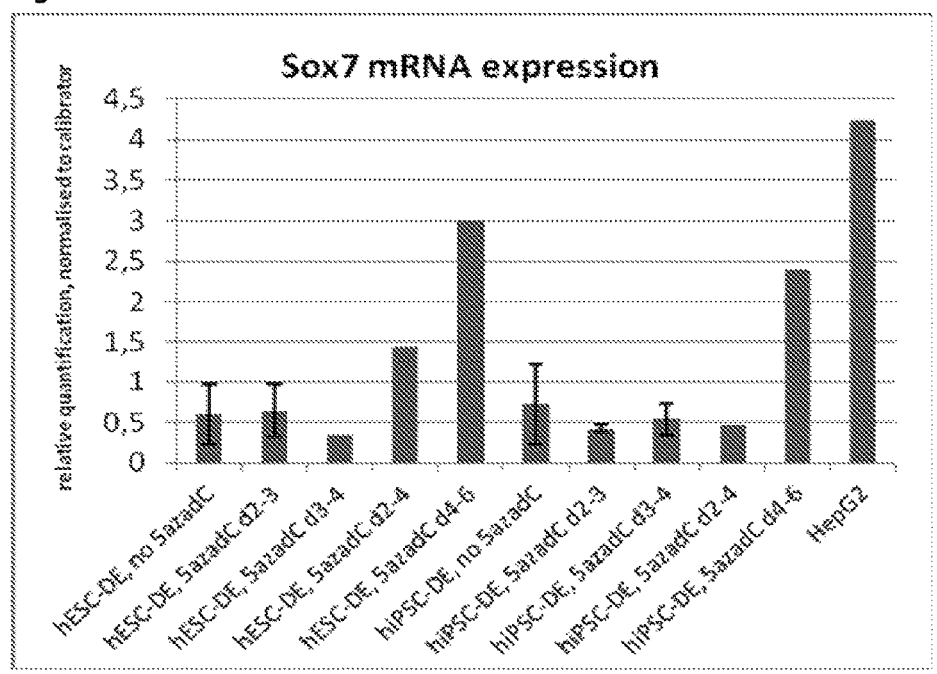

Results:

FIG. 1A: DE derived from hESC treated with 10nM 5-aza-2-deoxycytidine on day 2-3 (FIG. 1A2) is more homogeneous and has more pronounced cell-cell contacts compared to untreated control DE (FIG. 1A1). Note the presence of undifferentiated cells in the control DE (FIG. 1A1) which is in accordance with higher expression of Oct4 and Nanog mRNA expression in control DE (compare FIG. 1D). Similar results were obtained when treating cells on days 2-4, 3-4 and 4-6 and with 100 nM 5-aza-2-deoxycytidine. 1 nM 5-aza-2-deoxycytidine had less effect (data not shown).

FIG. 1B:

HiPSC-derived DE treated with 10 nM 5-aza-2-deoxycytidine on day 2-3 (FIG. 1B2) is more confluent and has more pronounced cell-cell contacts than control DE (FIG. 1B1). Similar results were obtained when treating cells days 2-4, 3-4 and 4-6 and with 100 nM 5-aza-2-deoxycytidine. 1 nM 5-aza-2-deoxycytidine had less effect (data not shown).

FIG. 1C:

HiPSC-derived DE treated with 10 nM 5-aza-2-deoxycytidine on day 2-3 has much less Oct4-immunopositive cells at day 7 compared to untreated controls, i.e. less undifferentiated cells are left and the DE is more homogeneous after treatment with a demethylating agent.

FIG. 1D:

Expression of the stem cell marker Oct4 is much lower in hESC- and hiPSC-derived DE treated with 10 nM 5azadC on day 2-3, 3-4, 2-4, and 4-6 than in untreated controls (FIG. 1D1). In 5azadC-treated hESC-derived DE mRNA expression of the stem cell marker Nanog is strongly decreased whereas it remains mainly unaffected in hiPSC-derived DE (FIG. 1D1). Expression of the DE markers Sox17, Cxcr4, FoxA2 and hHex is up-regulated in 5azadC-treated hESC- and hiPSC-derived DE compared to untreated controls while the effect is stronger in hESC-derived DE than in hiPSC-derived DE (FIG. 1D3-6). Expression of the extraembryonic marker Sox7 is very low both in control and 5azadC-treated hESC- and hiPSC-derived DE with the exception of 5azadC-treatment on days 2-4 and 4-6 which increases Sox7 mRNA levels.

Taken together, the treatment of the cells with a DNA demethylation agent during endodermal development led to improved DE morphology and DE cell yield in both hESC and hiPSC derived cells (FIG. 1A-B). Furthermore it resulted in a stronger decrease of the stem cell marker Oct4 as detected by immunocytochemistry (FIG. 1C), to an improved expression of well defined DE markers SOX17, CXCR4, HEX, Foxa2, as well as a decrease of the extra-embryonic endoderm marker Sox7 and of the stem markers Oct4 and Nanog (FIG. 1D). Therefore the skilled person wishing to produce a more homogeneous population of definitive endoderm cells can select from one or more DNA-demethylation agents and employ them e.g. at days 2-3 or 3-4 during differentiation of pluripotent stem cell types.

Example 4

Highly Homogeneous Definitive Endoderm Derived from a Panel of 27 hPSC Lines by Treatment with DNA Demethylating Agents During DE Differentiation Procedure: Following the basic protocols A or B, cells derived from 27 hPSC lines were treated with 10 nM 5-aza-2-deoxycytidine on day 2-3 during during the hPS differentiation into definitive endoderm (protocol A: ChiPSC14, ChiPSC19, ChiPSC22, P11015, SA167, SA181, SA461, and Va19; protocol B: ChiPSC4, ChiPSC6b, ChiPSC7, ChiPSC8, ChiPSC9, ChiPSC10, ChiPSC11, ChiPSC13, ChiPSC15, ChiPSC17, ChiPSC18, ChiPSC19, ChiPSC20, ChiPSC21, ChiPSC23, ChiPSC24, P11012, P11021, P11025, and SA121).

23 out of 27 hPSC lines were tested with both protocols A and B. Out of these 23 lines, only 4 cell lines (ChiPSC14, ChiPSC23, P11015, and P11032) could only be differentiated with one of the two protocols. Four hPSC lines (ChiPSC8, ChiPSC9, ChiPSC10, and ChiPSC11) were only tested with protocol B.

For analysis of mRNA expression, hESC- and hiPSC-derived DE-cells were harvested on day 7 of the protocol and gene expression was analysed using qRT-PCR, normalised to the house-keeping gene CREBBP, and the results presented as relative quantification normalised to a calibrator.

Figure 2A:
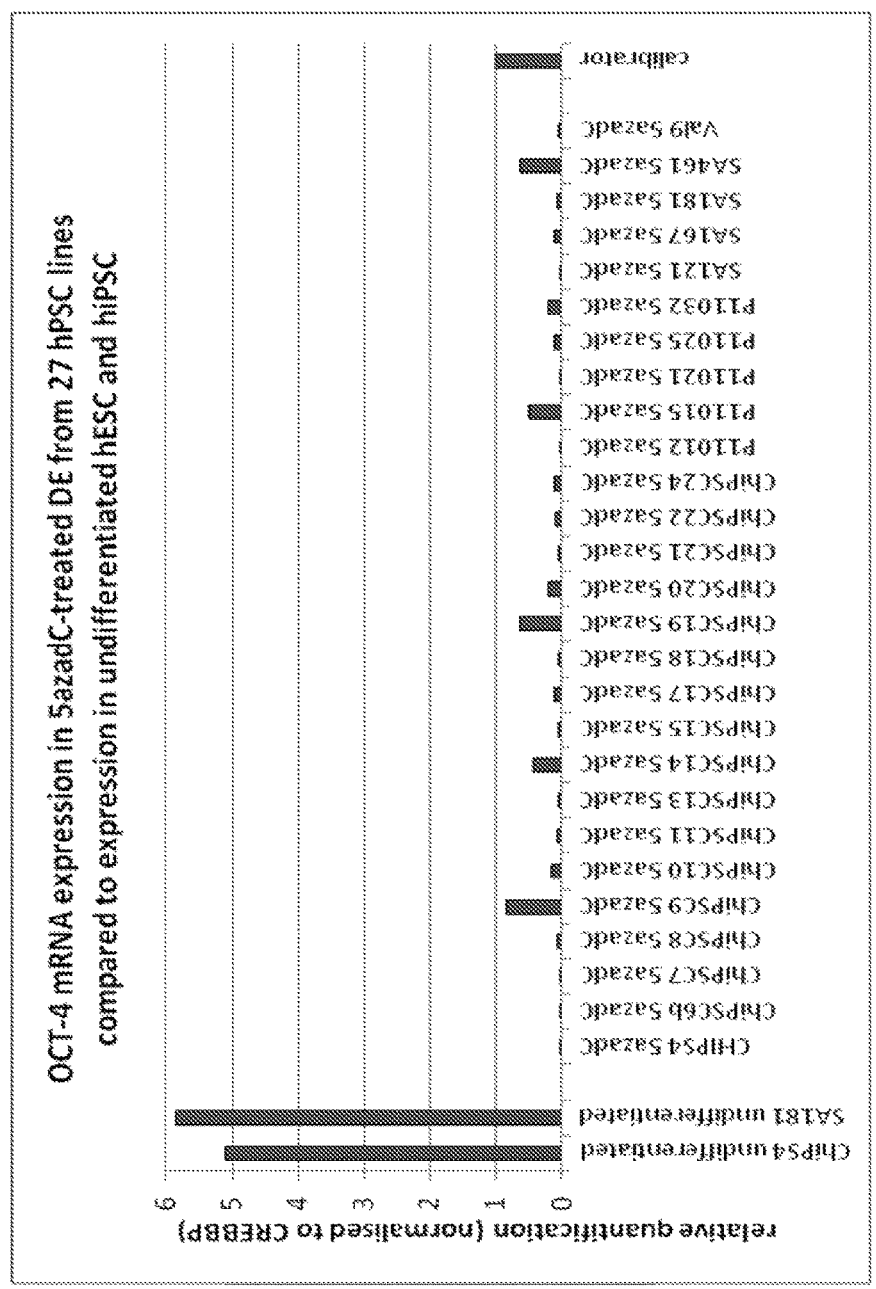
FIG. 2A. mRNA expression of stem cell marker Oct4 in definitive endodermal cells derived from 27 different hESC- and hiPSC lines (derived with basic protocols A and B, respectively) with a 5-aza-deoxycytidine treatment during the pre-endodermal phase (day 0-7 of the protocol).
Figure 2B:
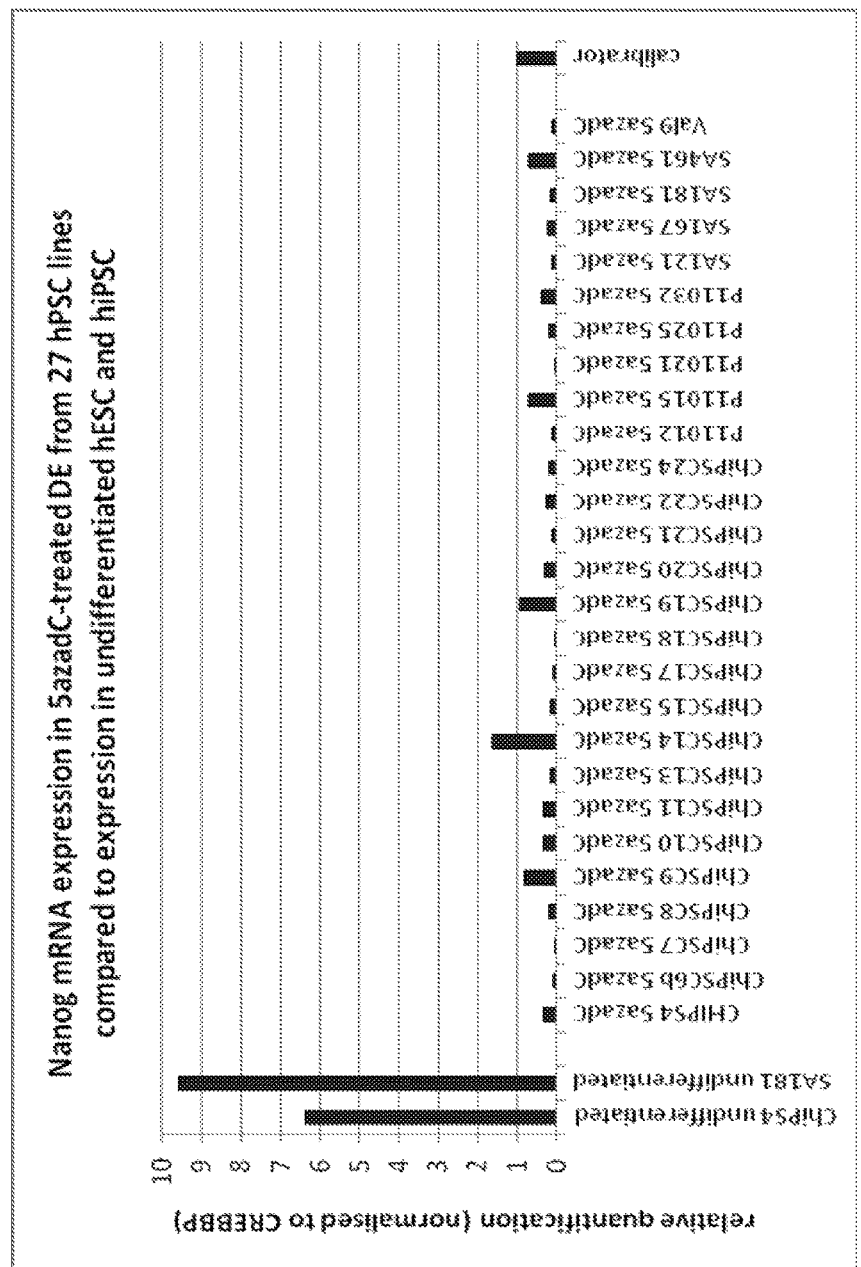
FIG. 2B. mRNA expression of stem cell marker Nanog in definitive endodermal cells derived from 27 different hESC- and hiPSC lines (derived with basic protocols A and B, respectively) with a 5-aza-deoxycytidine treatment during the pre-endodermal phase (day 0-7 of the protocol).
Figure 2C:
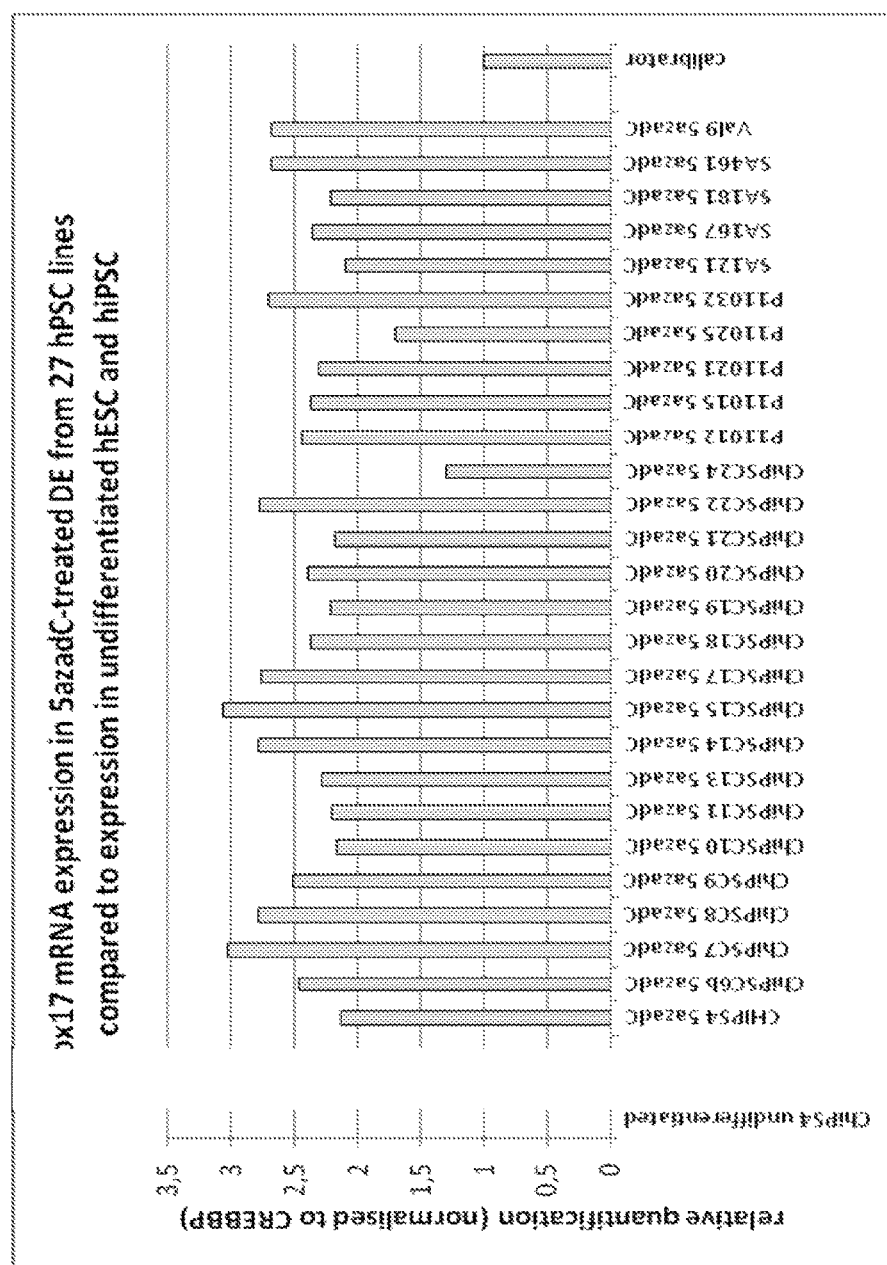
FIG. 2C. mRNA expression of DE marker Sox17 in definitive endodermal cells derived from 27 different hESC- and hiPSC lines (derived with basic protocols A and B, respectively) with a 5-aza-deoxycytidine treatment during the pre-endodermal phase (day 0-7 of the protocol).
Figure 2D:
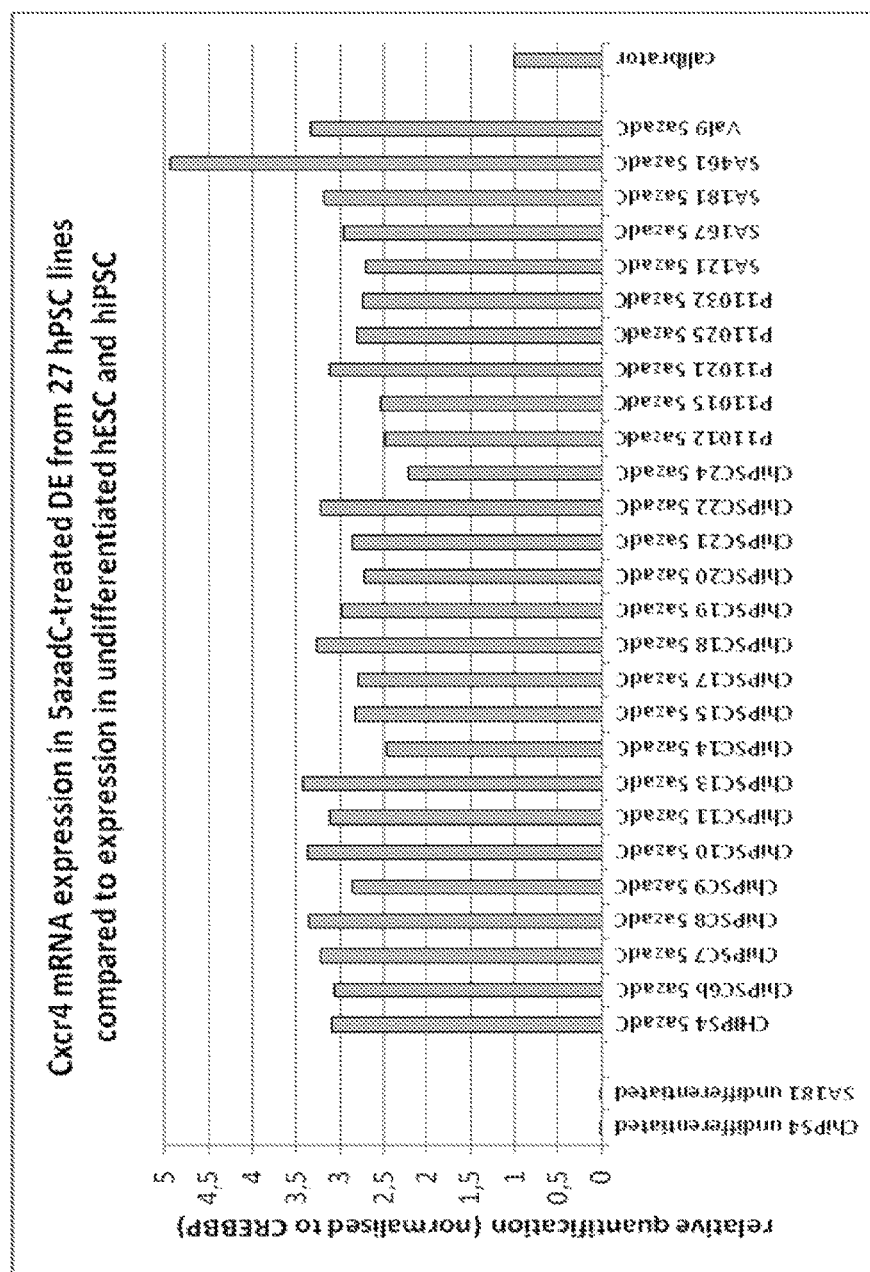
FIG. 2D. mRNA expression of DE marker Cxcr4 in definitive endodermal cells derived from 27 different hESC- and hiPSC lines (derived with basic protocols A and B, respectively) with a 5-aza-deoxycytidine treatment during the pre-endodermal phase (day 0-7 of the protocol).

Results:

FIG. 2A-D:

Using the basic protocols A or B including a DNA demethylating treatment on day 2-3 during the hPS differentiation into definitive endoderm, undifferentiated stem cells from 27 different hPSC lines could be differentiated into highly homogeneous DE displaying low mRNA expression levels of the stem cell markers Oct-4 and Nanog (FIG. 2A, B) and high levels of the DE markers Sox17 and Cxcr4 (FIG. 2C, D) compared to undifferentiated hESC (SA181) and hiPSC (ChiPSC4).

Taken together, the treatment of the cells during hPS differentiation into definitive endoderm with a DNA demethylating agent allows derivation of homogeneous DE with low expression levels of stem cell markers and high expression levels of DE markers from all hPSC lines tested. The derivation of homogeneous DE is crucial for derivation of homogeneous hepatocyte cultures which could be obtained from all lines tested (data not shown).

Therefore the skilled person wishing to produce a homogeneous population of definitive endoderm cells from any given hPSC line can include a treatment with a DNA demethylating agent, for instance, on day 2-3 during differentiation of hPS cells into definitive endodem.

Example 5

Both DNA Demethylating Agents 5-aza-2-deoxycytidine and 5-azacytidine Improve the Definitive Endoderm Phenotype in hESC- and hiPSC-Derived DE Procedure:

Following the basic protocols A (hPSC lines P11032, and SA181) or B (hPSC line P11012), cells derived from 3 different hPSC lines were treated with either 10 nM 5-aza-2-deoxycytidine or 1 µM 5-azacytidine on day 2-3 during the hPS differentiation into definitive endodem.

For analysis of mRNA expression, hESC- and hiPSC-derived DE-cells were harvested on day 7 of the protocol and gene expression was analysed using qRT-PCR, normalised to the house-keeping gene CREBBP, and the results presented as relative quantification normalised to a calibrator.

Figure 3A:
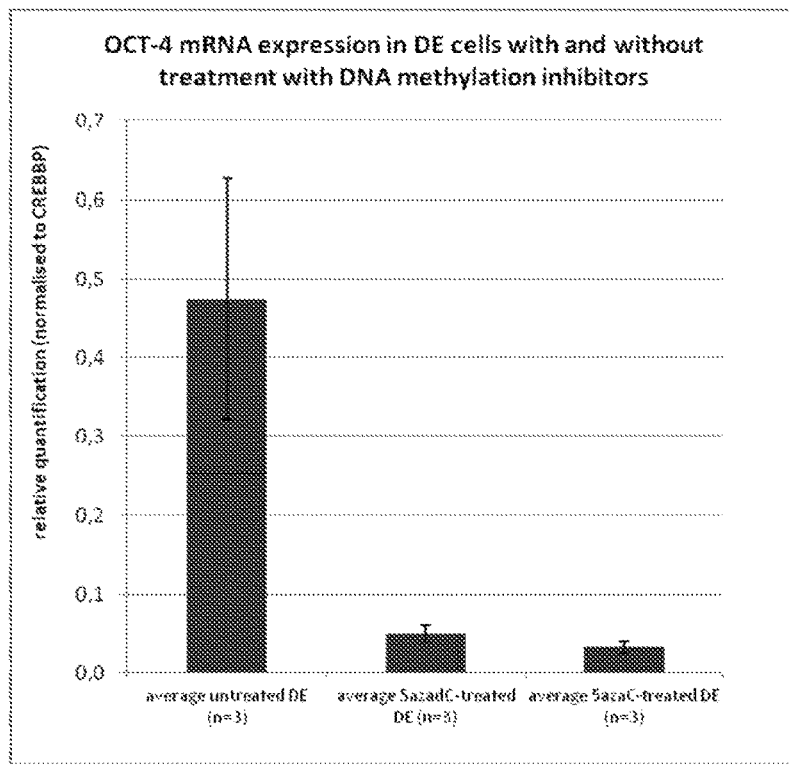
FIG. 3A. mRNA expression of stem cell marker Oct4 in definitive endodermal cells derived from 3 hESC- and hiPSC lines (derived with basic protocols A and B, respectively) with or without a treatment with 5-aza-deoxycytidine or 5-azacytidine during the pre-endodermal phase (day 0-7 of the protocol).
Figure 3B:
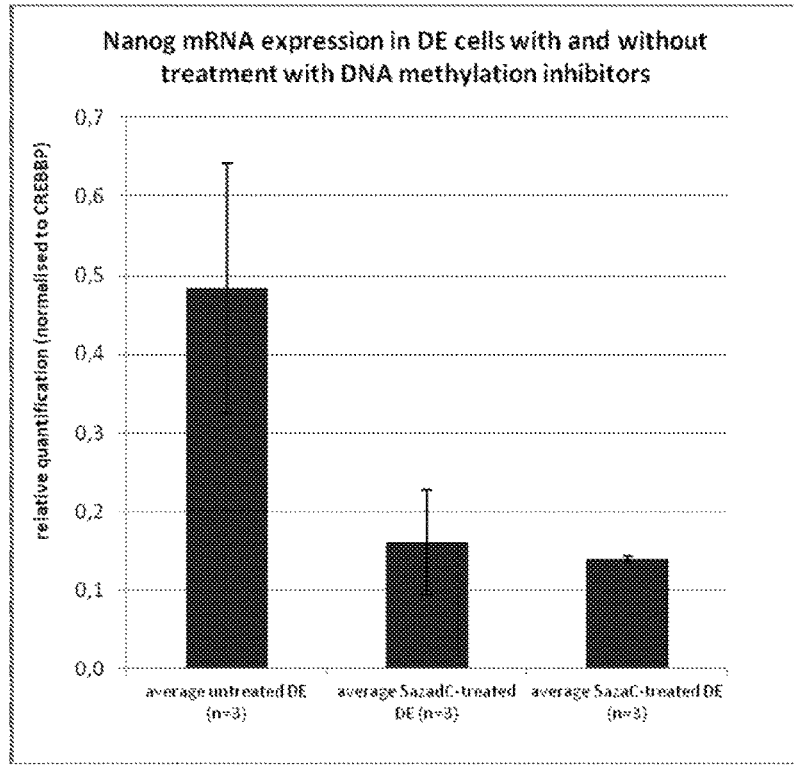
FIG. 3B. mRNA expression of stem cell marker Nanog in definitive endodermal cells derived from 3 hESC- and hiPSC lines (derived with basic protocols A and B, respectively) with or without a treatment with 5-aza-deoxycytidine or 5-azacytidine during the pre-endodermal phase (day 0-7 of the protocol).

Results:

FIG. 3:

A, B) Without treatment with a demethylating agent, the three hPSC lines P11032, SA181 and P11012 produced heterogeneous DE with relatively high mRNA expression of stem cell markers Oct4 and Nanog (FIG. 3A, B). Treatment with the DNA demethylating agents 5-aza-2-deoxycytidine (5azadC) and 5-azacytidine (5azaC) significantly decreased Oct4 and Nanog mRNA (FIG. 3A, B) and thus allowed derivation of a homogeneous DE population from these three hPSC lines.

Figure 3C:
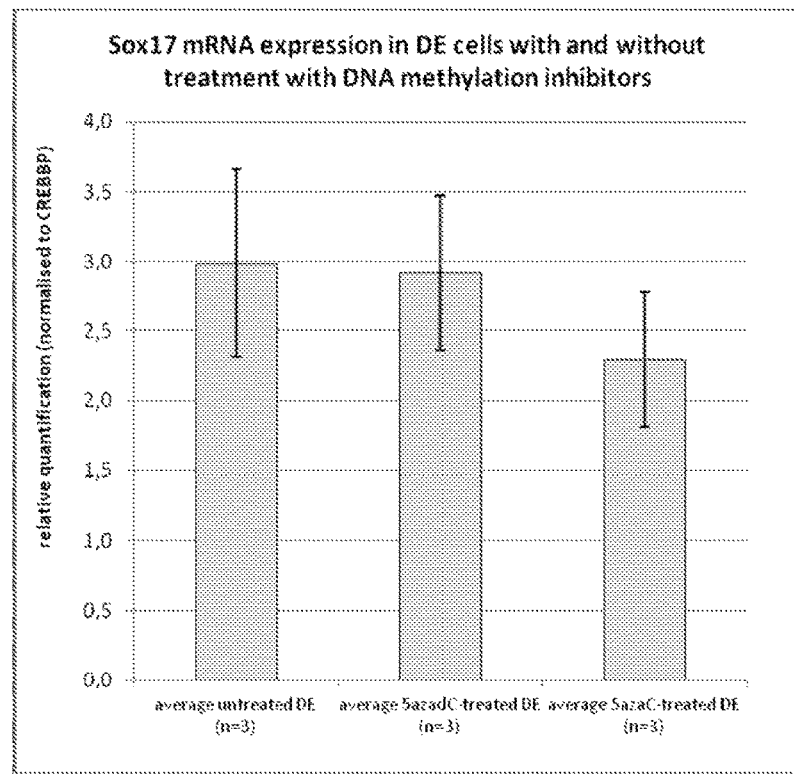
FIG. 3C. mRNA expression of DE marker Sox17 in definitive endodermal cells derived from 3 hESC- and hiPSC lines (derived with basic protocols A and B, respectively) with or without a treatment with 5-aza-deoxycytidine or 5-azacytidine during the pre-endodermal phase (day 0-7 of the protocol).
Figure 3D:
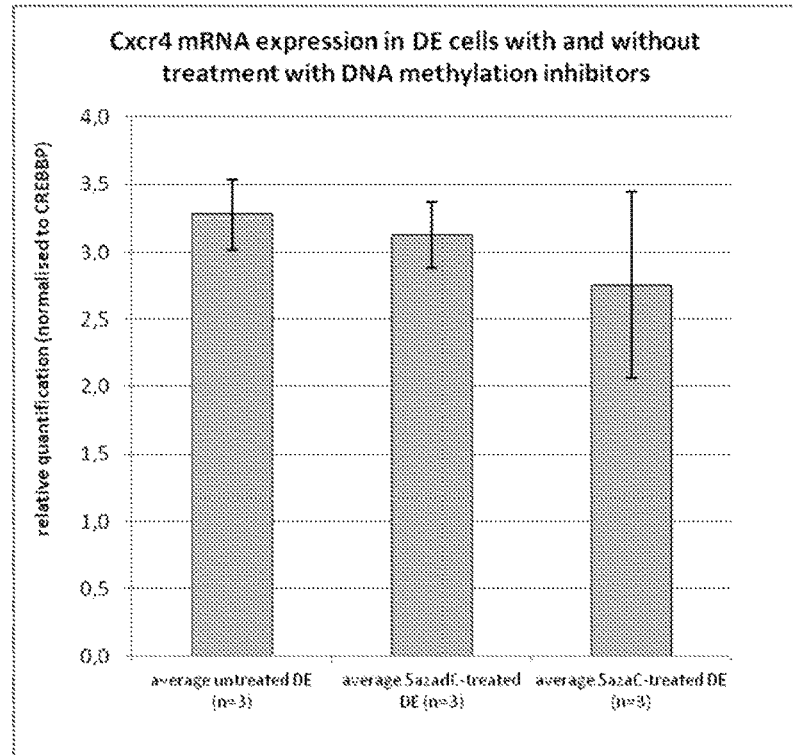
FIG. 3D. mRNA expression of DE marker Cxcr4 in definitive endodermal cells derived from 3 hESC- and hiPSC lines (derived with basic protocols A and B, respectively) with or without a treatment with 5-aza-deoxycytidine or 5-azacytidine during the pre-endodermal phase (day 0-7 of the protocol).

C, D) No significant changes in mRNA expression of the DE markers Sox17 and Cxcr4 could be observed upon treatment with 10 nM 5-aza-2-deoxycytidine or 1 µM 5-azacytidine (FIG. 3C, D).

Taken together, treatment with both DNA demethylating agents 5-aza-2-deoxycytidine (5azadC) and 5-azacytidine (5azaC) allows derivation of homogeneous DE from hPSC lines, giving otherwise heterogeneous DE if untreated.

Therefore the skilled person wishing to produce a homogeneous population of definitive endoderm cells can select from one or more DNA-demethylation agents and employ them e.g. at days 2-3 during differentiation of pluripotent stem cell types into definitive endodem.

REFERENCES

Brolen, G. et al. (2010) Hepatocyte-like cells derived from human embryonic stem cells specifically via definitive endoderm and a progenitor stage. J Biotechnol. 1; 145 (3):284-94

Chung, Y. et al. (2008) Human Embryonic Stem Cell Lines Generated without Embryo Destruction. doi: 10.1016/j.stem.2007.12.013

Duan, Y. et al. Differentiation and characterization of metabolically functioning hepatocytes from human embryonic stem cells. Stem Cells. 28(4):674-86

Hay, D. et al (2007) Direct differentiation of human embryonic stem cells to hepatocyte-like cells exhibiting functional activities. Cloning Stem Cells. 2007 Spring; 9(1): 51-62. Erratum in: Cloning Stem Cells. 2009 March; 11(1):209.

Hay, D. et al (2008) Efficient differentiation of hepatocytes from human embryonic stem cells exhibiting markers recapitulating liver development in vivo. Stem Cells. April; 26(4):894-902.

Heins, N. et al (2004) Derivation, characterization, and differentiation of human embryonic stem cells. Stem Cells. 22(3):367-76.

Klimanskaya, I. et al (2006) Human embryonic stem cell lines derived from single blastomeres. Nature, November 23; 444(7118):481-5. Epub 2006 Aug. 23. Erratum in: Nature. 2006 Nov. 23; 444(7118):512. Nature. 2007 Mar. 15; 446(7133):342.

Martin M. et al (2005) Human embryonic stem cells express an immunogenic nonhuman sialic acid. Nat Med. February; 11(2):228-32.

Mercader, A. et al (2009) Human Embryo Culture. Essential Stem Cell Methods, Chapter 16, Academic Press, 1$^{st}$ Edition, Eds. Lanza, R. and Klimanskaya, I.

Takahashi, K. et al (2007) Induction of pluripotent stem cells from adult human fibroblasts by defined factors. Cell November 30; 131(5):861-72.

Thomson, J. et al. (1998) Embryonic stem cell lines derived from human blastocysts. Science. November 6; 282 (5391):1145-7. Erratum in: Science 1998 Dec. 4; 282 (5395):1827.

Yoon, BS et al. (2006) Enhanced differentiation of human embryonic stem cells into cardiomyocytes by combining hanging drop culture and 5-azacytidine treatment. Differentiation. 74(4):149-59.

Yu, J. and Thomson, J. (2009) Induced Puripotent Stem Cell Derivation. Essentials of Stem Cell Biology, Chapter 37, Academic Press, 2$^{nd}$ Edition (2009), Eds. Lanza, R. et al.

Zhou H. et al (2009). Generation of induced pluripotent stem cells using recombinant proteins. Cell Stem Cell. 4(5): 381-4.

The invention claimed is:

1. A method for producing definitive endodermal cells (DE cells) from mammalian pluripotent stem cells, the method comprising:
    differentiating mammalian pluripotent stem cells under directed differentiation conditions to obtain a cell composition which is characterized in that at least 70% of the cells are DE cells, and
    exposing the mammalian pluripotent stem cells to a nucleoside-analogue type DNA demethylating agent while undergoing differentiation, wherein the exposing of the mammalian pluripotent stem cells to the nucleoside-analogue type DNA demethylating agent first takes place on day 2 of differentiation, and wherein the cell composition obtained shows increased gene expression of sox17, cxcr4 and hhex compared to a cell composition obtained without exposure to the nucleoside-analogue type DNA demethylating agent.

2. The method according to claim 1, wherein the mammalian pluripotent stem cells are human pluripotent stem cells, primate pluripotent stem cells, mouse pluripotent stem cells, rat pluripotent stem cells, canine pluripotent stem cells, feline pluripotent stem cells, porcine pluripotent stem cells, bovine pluripotent stem cells or equine pluripotent stem cells.

3. The method according to claim 1, wherein the mammalian pluripotent stem cells are not human pluripotent stem cells.

4. The method according to claim 1, wherein the mammalian pluripotent stem cells are mammalian embryonic stem cells.

5. The method according to claim 1, wherein the mammalian pluripotent stem cells are mammalian induced pluripotent stem cells.

6. The method according to claim 1, wherein the mammalian pluripotent stem cells are human pluripotent stem (hPS) cells.

7. The method according to claim 6, wherein the human pluripotent stem cells are human embryonic stem (hES) cells.

8. The method according to claim 7, wherein the human embryonic stem cells have been obtained without destruction of a human embryo.

9. The method according to claim 6, wherein the human pluripotent stem cells are human induced pluripotent stem (hiPS) cells.

10. The method according to claim 1, wherein the nucleoside-analogue type DNA demethylating agent is a cytidine analogue.

11. The method according to claim 1, wherein the nucleoside-analogue type DNA demethylating agent is selected from the group consisting of: 5-aza-2-deoxycytidine (decitabine), 5-azacytidine (azacitidine), zebularine, Pseudoisocytidine, 5-fluoro-2-deoxycytidine, 5,6-dihydro-5-azacytidine, 2'-deoxy-5,6-dihydro-5-azacytidine, 6-azacytidine, 2',2'-Difluoro-deoxycytidine (gemcitabine), or Cytosine-beta-D-arabinofurasonide.

12. The method according to claim 1, wherein the nucleoside-analogue type DNA demethylating agent is a cytidine analogue selected from the group consisting of 5-aza-2-deoxycytidine (decitabine), 5-azacytidine (azacitidine), 5-fluoro-2-deoxycytidine, 5,6-dihydro-5-azacytidine, 2'-deoxy-5,6-dihydro-5-azacytidine, 6-azacytidine and 2',2'-Difluoro-deoxycytidine (gemcitabine).

13. The method according to claim 1, wherein the nucleoside-analogue type DNA demethylating agent is selected from the group consisting of: 5-aza-2-deoxycytidine (decitabine), 5-azacytidine (azacitidine), zebularine, and combinations thereof.

14. The method according to claim 1, wherein said differentiation conditions for obtaining DE cells are characterized by culturing the mammalian pluripotent stem cells in a differentiation medium comprising activin and optionally one or more growth factors or serum.

15. The method according to claim 1, wherein said differentiation conditions for obtaining cells of the definitive endoderm are further characterized by culturing the mammalian pluripotent stem cells for up to 10 days in differentiation medium.

16. The method according to claim 1, wherein the exposing of the mammalian pluripotent stem cells to the nucleoside-analogue type DNA demethylating agent takes place on day 2 to day 3 or on day 2 to day 4 of differentiation.

17. The method according to claim 1, wherein the exposing of the mammalian pluripotent stem cells to the nucleoside-analogue type DNA demethylating agent takes place on day 2 to day 3 of differentiation.

18. The method according to claim 1, wherein the nucleoside-analogue type DNA demethylating agent is 5-aza-2-deoxycytidine (decitabine).

19. The method according to claim 18, wherein 5-aza-2-deoxycytidine is employed at a concentration in the range of 1 nM to 500 nM.

20. The method according to claim 18, wherein 5-aza-2-deoxycytidine is employed at a concentration in the range of 5 nM to 100 nM.

21. The method according to claim 1, wherein the nucleoside-analogue type DNA demethylating agent is 5-azacytidine (azacitidine).

22. The method according to claim 21, wherein 5-azacytidine is employed at a concentration in the range of 1 nM to 1 μM.

23. The method according to claim 1, wherein the nucleoside-analogue type DNA demethylating agent is 5-aza-2-deoxycytidine (decitabine) which is employed at a concentration in the range of 5 nM to 100 nM, and wherein the exposing of the mammalian pluripotent stem cells to 5-aza-2-deoxycytidine takes place on day 2 to day 3 or on day 2 to day 4 of differentiation.

24. The method according to claim 1, wherein the nucleoside-analogue type DNA demethylating agent is 5-aza-2-deoxycytidine (decitabine) which is employed at a concentration in the range of 5 nM to 100 nM, and wherein the exposing of the mammalian pluripotent stem cells to 5-aza-2-deoxycytidine takes place on day 2 to day 3 of differentiation.

* * * * *